United States Patent [19]

Powell et al.

[11] Patent Number: 5,125,954
[45] Date of Patent: Jun. 30, 1992

[54] HERBICIDAL OXABICYCLOALKANE ETHERS

[75] Inventors: James E. Powell, Rising Sun, Md.; Richard B. Phillips, Irvine, Calif.

[73] Assignee: E.I. Du Pont de Nemours and Company, Wilmington, Del.

[21] Appl. No.: 601,802

[22] PCT Filed: May 18, 1989

[86] PCT No.: PCT/US89/02091
 § 371 Date: Nov. 2, 1990
 § 102(e) Date: Nov. 2, 1990

[87] PCT Pub. No.: WO89/11481
 PCT Pub. Date: Nov. 30, 1989

Related U.S. Application Data

[63] Continuation-in-part of Ser. No. 197,181, May 23, 1988, abandoned.

[51] Int. Cl.⁵ .................. A01N 43/08; C07D 493/08
[52] U.S. Cl. ........................... 71/88; 546/141; 546/142; 546/153; 546/155; 546/158; 518/460; 549/9; 549/23; 549/52; 549/54; 549/55; 549/56; 549/88; 549/332; 549/345; 549/354; 549/397; 549/399; 549/400; 549/401; 549/463; 549/510; 549/511
[58] Field of Search ................ 549/463; 71/88

[56] References Cited

U.S. PATENT DOCUMENTS

| | | |
|---|---|---|
| 4,388,104 | 6/1983 | Powell et al. .................. 549/397 |
| 4,525,203 | 6/1985 | Payne et al. .................... 549/397 |
| 4,554,365 | 11/1985 | Mulder ........................... 549/463 |
| 4,588,821 | 5/1986 | Powell et al. .................. 549/397 |

FOREIGN PATENT DOCUMENTS

WO89/11481 11/1989 PCT Int'l Appl. ............ 549/463

*Primary Examiner*—C. Warren Ivy
*Assistant Examiner*—James H. Turnipseed
*Attorney, Agent, or Firm*—Susan B. Evans

[57] ABSTRACT

The present invention relates to novel bicyclo ether derivatives, to compositions containing them, and to their method of use especially to control the growth of undesired vegetation in rice.

9 Claims, No Drawings

HERBICIDAL OXABICYCLOALKANE ETHERS

RELATED APPLICATION

This application is a continuation-in-part of my co-pending application U.S. Ser. No. 07/197,181, filed May 23, 1988, now abandoned.

BACKGROUND OF THE INVENTION

1. Field of the Invention

The present invention relates to novel bicyclo ether derivative compounds, to compositions containing these ether derivative compounds, and to methods of using these compounds or compositions to control the growth of undesired vegetation.

2. Description of Related Art

Vieira et al., *Helvetica Chimica Acta*, 65(6) (1982), pp. 1700-06, teach the preparation of the oxabicyclic cyanohydrin acetates via a Diels-Alder reaction.

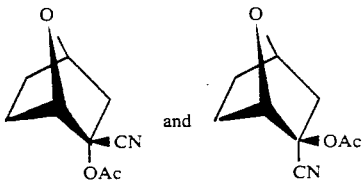

Vieria et al., *Helvetica Chimica Acta*, 66(6) (1983), pp. 1865-71 teach a chiral variant of the above described reaction which produces oxabicyclic cyanohydrin esters homologous to those depicted above, but with a (−)-camphanoyl group instead of an acetate group.

Black et al., *Helvetica Chimica Acta*, 67 (1984), pp. 1612-15, disclose a method for the preparation of the chiral oxabicyclic ketone via diastereoselective formation of a brucine complex of the corresponding cyanohydrin acetate.

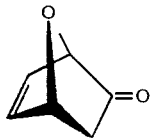

Payne et al., U.S. Pat. No. 4,567,283 and Payne et al., U.S. Pat. No. 4,670,041 disclose a variety of herbicidal bicyclic ethers of the Formula

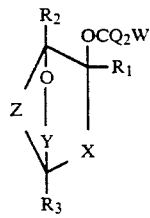

wherein
W is an unsaturated, aromatic or heterocyclic group. This reference also disclosed certain bicyclic and monocyclic intermediates to these compounds.

Payne et al., U.S. Pat. No. 4,525,203, disclose herbicidal bicyclic ethers of the Formula

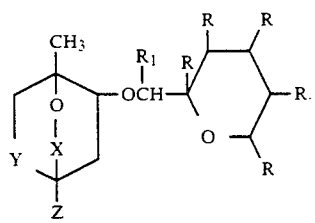

GB 2188-931 discloses compounds of the following formula as herbicides:

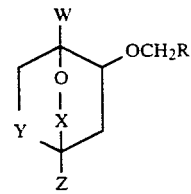

SUMMARY OF THE INVENTION

This invention pertains to compounds of Formula I including stereoisomers, suitable agricultural compositions containing them and their use as broad spectrum preemergent and postemergent herbicides.

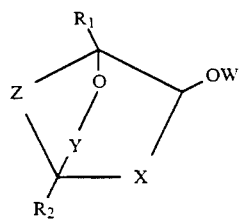

(I)

wherein:
- X is $(CH_2)_m$;
- Y is $(CR_3R_4)_p$;
- Z is $(CR_3R_4)_n$;
- p is 0 to 2;
- m is 0 to 2;
- n is 1 to 3;
- $R_1$ is H or a straight-chain $C_1$-$C_3$ alkyl;
- $R_2$ is H, $C_1$-$C_6$ alkyl, $C_2$-$C_4$ alkenyl, $C_2$-$C_4$ alkynyl, phenyl or $C_1$-$C_4$ alkyl substituted by halogen, Ph, OH, CN, $OR_a$, $SO_2R_a$, $PhSO_2$, $N_3$, $CO_2R_a$, or $CO_2H$;
- $R_3$ is H or $C_1$-$C_3$ alkyl;
- $R_4$ is H or $CH_3$;
- $R_3$ and $R_4$ may be taken together to form a 5- or 6-membered carbocyclic ring;
- W is

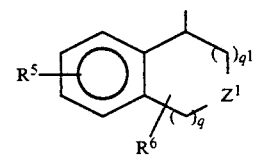

$Z^1$ is $CH_2$, $NR_3$, O, S or may be taken to form a double bond with an adjacent carbon;
$R_5$ is H, halogen, $R_a$, $OR_a$, $SR_a$ or CN;

$R_6$ is H, F, Cl, $CH_3$, $OCH_3$, OH or $OR_a$;
$R_a$ is $C_1$-$C_3$ alkyl;
$q^1$ is 0, 1 or 2; and
q is 0 to 2
provided that the sum of q and $q^1$ is 0, 1 or 2 and that if q and $q^1$ is O then $Z^1$ is $CH_2$.

Preferred for either their biological activity or ease of synthesis are:

1. Compounds of Formula I wherein;
   $R_2$ is $C_1$-$C_3$ alkyl, $C_2$-$C_3$ alkenyl, $C_2$-$C_3$ alkynyl, or $C_1$-$C_2$ alkyl substituted by OH, CN, $OCH_3$, $SO_2CH_3$, $SO_2Ph$ or $CO_2CH_3$; and
   $R_5$ is H, F, Cl, Br, $CH_3$, $OCH_3$, $SCH_3$ or CN.
2. Compounds of Preferred 1 wherein;
   n is 2;
   m is 1;
   p is 0; and
   $R_3$ is H or $CH_3$.
3. Compounds of Preferred 1 wherein;
   n is 3;
   m is 2;
   p is 0; and
   $R_3$ is H or $CH_3$.
4. Compounds of Preferred 1 wherein;
   n is 1;
   m is 2;
   p is 1; and
   $R_3$ is H or $CH_3$.
5. Compounds of Preferred 2, 3 or 4 wherein;
   $Z^1$ is $CH_2$.
6. Compounds of Preferred 2, 3 or 4 wherein;
   $Z^1$ is O.
7. Compounds of Preferred 2, 3 or 4 wherein;
   $Z^1$ is S.
8. Compounds of Preferred 2, 3 or 4 wherein;
   $Z^1$ is $NR_3$.
9. Compounds of Preferred 2, 3 or 4 wherein;
   W is

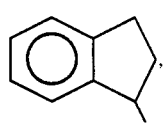 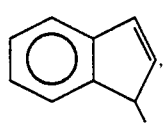 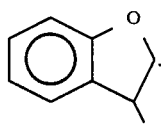

W-1  W-2  W-3

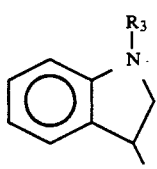 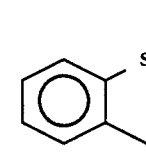 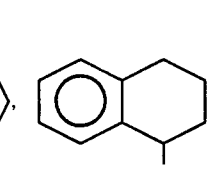

W-4  W-5  W-6

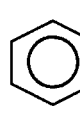 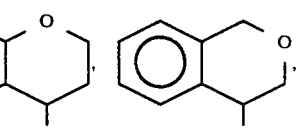

W-7  W-8

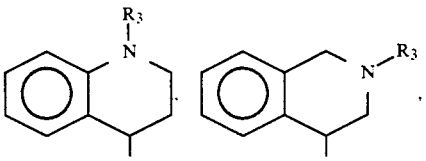

W-9  W-10

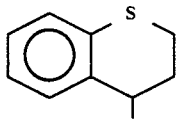

W-11  W-12

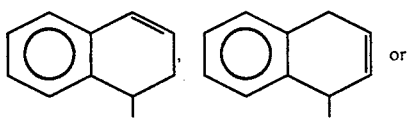

W-13  W-14

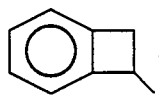

W-15

Specifically preferred are:
exo-2-(2,3-dihydro-1H-inden-1-yloxy)-1-methyl-4-(1-methylethyl)-7-oxabicyclo((2.2.1))heptane; and
exo-2-(2,3-dihydro-1H-inden-1-yloxy)-1,4-diethyl-7-oxabicyclo[2.2.1]heptane.

DETAILED DESCRIPTION OF THE INVENTION

The compounds of Formula I exhibit geometrical and optical isomerism and may be prepared in geometrically or optically pure or mixed forms. The various individual optical and geometrical forms and various combinations thereof of the materials of the invention usually have some difference in herbicidal properties. Generally preferred for herbicidal efficacy are 1) those geometrical isomers of Formula I wherein the OW group resides on the same face of the carbocyclic ring as the O-Y bridge and 2) those optical isomers with the absolute configuration depicted in Formula Ia. The present invention contemplates all of the herbicidally active forms resulting from synthesis and from deliberately created mixtures.

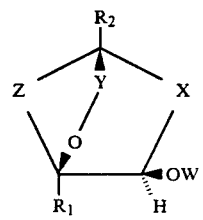

Formula Ia

The compounds of Formula Ia may be synthesized according to the well known Williamson Ether Synthesis (see N. Baggett in *Comprehensive Organic Chemistry*, D. Barton and W. D. Ollis eds., Vol. 1, pp. 819–832, Pergamon Press, New York (1979)) as shown in Scheme I by allowing bicyclic alcohols of Formula IV to react with appropriate alkylating agents represented as W-L where W represents those organic radicals defined previously and LG represents leaving group moieties such as chloride, bromide, iodide, and sulfonate esters. This is outlined in Scheme I.

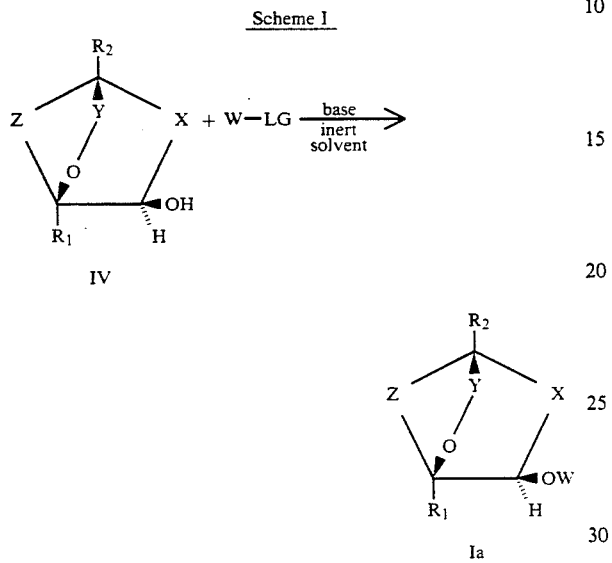

The bicyclic alcohols of Formula IV are known in the art (U.S. Pat. Nos. 4,670,041; 4,529,806; 4,486,219) and the alkylating agents W-LG are prepared in the conventional manners known to those skilled in the art from the alcohols W-OH.

The alcohols, WOH, are generally known in the art and are most conveniently prepared through metal hydride (e.g., sodium borohydride) reduction of the corresponding bicyclic ketones which can be derived by Friedel-Crafts type cyclization of derivatives of phenylalkylcarboxylic acid, phenoxyalkylcarboxylic acids, phenylthioalkylcarboxylic acids, benzyloxyalkylcarboxylic acids, and benzylthioalkylcarboxylic acids. Details may be found in a) T. Laird in *Comprehensive Organic Chemistry*, D. Barton and W. D. Ollis, eds., Vol. 1, pp. 1165–1168, Pergamon Press, New York (1979); b) M. H. Palmer and N. M. Scollick, *J. Chem. Soc., C.*, (1968), 2833; c) C. E. Dalgliesch and Mann, *J. Chem. Soc.*, (1945), 893; d) C. D. Hurd and S. Hayao, *J. Am. Chem. Soc.*, (1954), 76, 4299 and 5056; and e) R. Lesser, *Chem. Ber.*, (1923), 56, 1642.

Alternatively, the compounds of Formula Ia may be prepared by the coupling procedure described in Scheme II, which is used in cases where the standard Williamson ether synthesis proves problematic. This procedure uses a Lewis acidic metal oxide wherein the metal can remove the halide ion by forming an insoluble precipitate. In Example 1, silver (I) oxide is used and the silver halide is the co-product. Alternative metal oxides that may be used are HgO, CaO, MgO. N,N-Dimethylformamide and ethereal solvents, such as diethyl ether, tetrahydrofuran, dioxane, or 1,2-dimethoxyethane are the preferred solvents. Other solvents likely to provide good yields include dipolar aprotic solvents like dimethyl sulfoxide, acetone and N,N'-dimethylpropyleneurea.

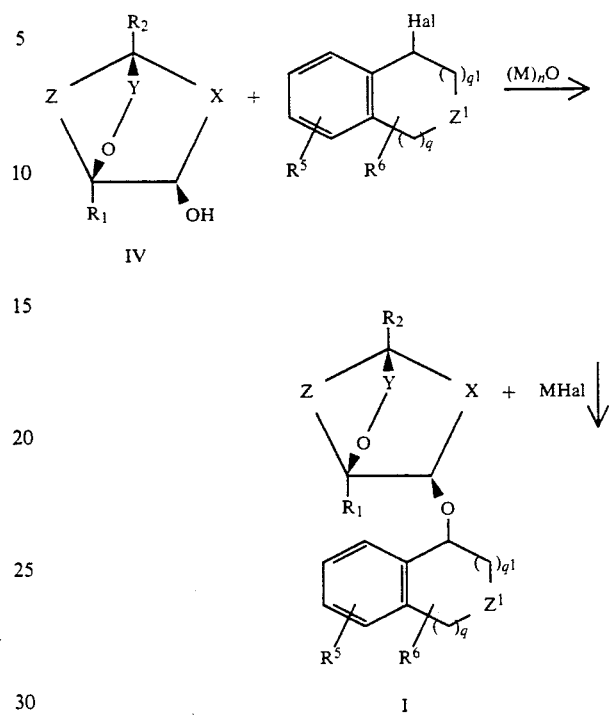

n is 1 or 2

The synthetic procedure shown in Scheme III may be used to prepare compounds of Formula Ia wherein $Z_1$ is a heteroatom (such as N, O, S). The coupling substrate is a styrene with an appropriate substituted heteroatom in protected form (such as with a trialkylsilyl, acetate ester, benzoate ester, etc.). A mild halogenating agent such as N-halosuccinimide, N-haloacetamide, dioxane dihalide, or pyridinium hydrohalide perhalide may be used to form a cyclic halonium ion under optional acid catalysis. The ion is intercepted at the benzylic center to form the benzylic ether. The heteroatom is deprotected and allowed to close in situ to form the desired heterocyclic ring. The acid catalyst for the initial coupling can be used in either concentrated or diluted form.

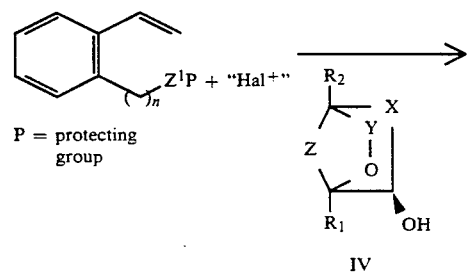

-continued
Scheme III

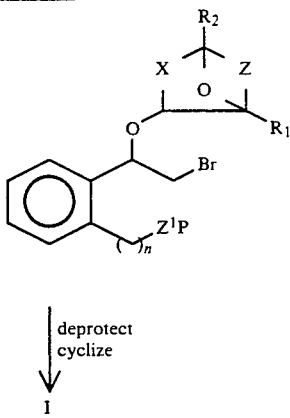

n is 0 or 1

EXAMPLE 1

(±)-exo-2-(2,3-Dihydro-1H-inden-2-yl-oxy)-1-methyl-4-(1-methylethyl)-7-Oxabicyclo[2.2.1]heptane (±)-Exo-1-methyl-4-(1-methylethyl)-7-oxabicyclo[2.2.1]heptane-2-ol (2.51 g, 14.7 mmoles) was dissolved in 7.3 mL of diethyl ether in a one-neck flask. 1-chloroindane (3.37 g, 22.1 mmoles) was then added, followed by silver (I) oxide (Aldrich, 3.41 g, 16.2 mmoles). A reflux condenser was fitted to the flask and the reaction was heated at reflux for 12 hrs. The mixture was allowed to cool and filtered through a pad of Celite Florisil or $SiO_2$. The filter cake was washed with diethyl ether, the filtrate was concentrated and chromatographed on $SiO_2$ (10–20% $Et_2O$/hexane) to obtain 2.12 g (51%) of the desired product as an oil in a 1:1 mixture of diastereomers.

$^1$H-NMR (CDCl$_3$, 200 MHz): 7.40 (m, 1H); 7.23 (m, 3H); 4.95 (app.t, 1H); 3.75 (m, 1H); 3.10 (m, 1H); 2.80 (m, 1H); 2.50–2.00 (m, 4H); 2.80–2.40 (m, 8H); 1.05 (2d, 6H).

EXAMPLE 2

Exo-2-[2,3-dihydrobenzofuran-3-yl-oxy]-1-methyl-4-(1-methylethyl)-7-oxabicyclo[2.2.1]heptane 2-ethenyl phenol was synthesized according to the procedure of Corson et al. (J. Org. Chem., 1958, 23, 544) and silated by standard procedures. 2-t-butyldimethylsiloxy styrene (550 mg, 2.03 mmoles) was dissolved in tetrahydrofuran (4.0 mL). Exo-1-methyl-4-(1-methylethyl)-7-oxabicyclo[2.2.1]heptane-2-ol (690 mg, 4.06 mmoles) and N-bromosuccinimide were added. One drop of perchloric acid (70%) was added. The reaction was stirred for 1½ hrs after which time a 1M solution of tetrabutylammonium fluoride in THF (2.5 mL) (any fluoride source, such as KF, NaF, $CaF_2$, HF will suffice) was added and the solution was stirred for an hour. The reaction mixture was diluted with diethyl ether and washed with $H_2O$. The organic layer was dried over anhydrous $Na_2SO_4$, filtered, and concentrated. It was then chromatographed on $SiO_2$ (10–20% $Et_2O$/hexane) to obtain 210 mg of the desired product in about 95% purity.

$^1$H-NMR (CDCl$_3$, 200 MHz): 7.30 (m, 1H); 7.25 (app. tdd, 1H); 6.90 (m, 2H); 5.10 (td, 1H); 4.85 (m, 2H); 3.70 (2dd, 1H); 2.15–1.90 (m, 2H); 1.70–1.30 (m, 8H); 0.98 (2d, 6H).

By the general procedures described, or by obvious modifications thereof, the compounds of Tables 1 to 8 can be prepared.

GENERAL STRUCTURE FOR TABLES 1 TO 6

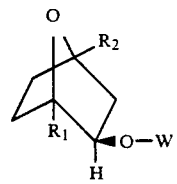

TABLE 1

$W = R_5$ (aryl structure shown with positions 4,5,6,7 and $Z_1$, 2, 3)

| $R_1$ | $R_2$ | $Z_1$ | $R_5$ |
|---|---|---|---|
| CH$_3$ | CH$_3$ | CH$_2$ | H |
| CH$_3$ | CH$_3$ | CH$_2$ | 4-F |
| CH$_3$ | CH$_3$ | CH$_2$ | 4-Cl |
| CH$_3$ | CH$_3$ | CH$_2$ | 4-CH$_3$ |
| CH$_3$ | CH$_3$ | CH$_2$ | 6-F |
| CH$_3$ | C$_2$H$_5$ | CH$_2$ | H |
| CH$_3$ | C$_2$H$_5$ | CH$_2$ | 4-F |
| CH$_3$ | C$_2$H$_5$ | CH$_2$ | 6-F |
| CH$_3$ | i-C$_3$H$_7$ | CH$_2$ | H |
| CH$_3$ | i-C$_3$H$_7$ | CH$_2$ | 4-F |
| CH$_3$ | i-C$_3$H$_7$ | CH$_2$ | 6-F |
| CH$_3$ | i-C$_3$H$_7$ | CH$_2$ | 4-Cl |
| CH$_3$ | i-C$_3$H$_7$ | CH$_2$ | 4-CH$_3$ |
| CH$_3$ | i-C$_3$H$_7$ | CH$_2$ | 4-OCH$_3$ |
| CH$_3$ | i-C$_3$H$_7$ | CH$_2$ | 4-SCH$_3$ |
| CH$_3$ | i-C$_3$H$_7$ | CH$_2$ | 5-CN |
| CH$_3$ | CCl(CH$_3$)$_2$ | CH$_2$ | H |
| CH$_3$ | CCl(CH$_3$)$_2$ | CH$_2$ | 4-F |
| CH$_3$ | C(CH$_3$)$_2$SO$_2$CH$_3$ | CH$_2$ | H |
| CH$_3$ | C(CH$_3$)$_2$OCH$_3$ | CH$_2$ | H |
| CH$_3$ | C(CH$_3$)$_2$CN | CH$_2$ | H |
| CH$_3$ | C(CH$_3$)$_2$OH | CH$_2$ | 4-Br |
| CH$_3$ | C(CH$_3$)$_2$OH | CH$_2$ | H |
| CH$_3$ | C(CH$_3$)$_2$SO$_2$Ph | CH$_2$ | H |
| CH$_3$ | Ph | CH$_2$ | H |
| CH$_3$ | H | CH$_2$ | H |
| CH$_3$ | CH$_2$CO$_2$CH$_3$ | CH$_2$ | H |
| CH$_3$ | CH$_2$CO$_2$H | CH$_2$ | 4-F |
| CH$_3$ | CH$_2$Ph | CH$_2$ | H |
| CH$_3$ | CH$_2$CH=CH$_2$ | CH$_2$ | H |
| CH$_3$ | CH$_2$CH=CH$_2$ | CH$_2$ | 4-F |
| CH$_3$ | C(CH$_3$)=CH$_2$ | CH$_2$ | H |
| CH$_3$ | CH$_2$C(CH$_3$)=CH$_2$ | CH$_2$ | H |
| CH$_3$ | CH$_2$C≡CH | CH$_2$ | H |
| C$_2$H$_5$ | CH$_2$C≡CH | CH$_2$ | H |
| C$_2$H$_5$ | CH$_2$CH=CH$_2$ | CH$_2$ | 4-F |
| C$_2$H$_5$ | CH$_2$CH=CH$_2$ | CH$_2$ | H |
| C$_2$H$_5$ | C$_2$H$_5$ | CH$_2$ | 4-F |
| C$_2$H$_5$ | C$_2$H$_5$ | CH$_2$ | 4-Cl |
| C$_2$H$_5$ | C$_2$H$_5$ | CH$_2$ | 6-F |
| C$_2$H$_5$ | C$_2$H$_5$ | CH$_2$ | 4-CH$_3$ |
| C$_2$H$_5$ | C$_2$H$_5$ | CH$_2$ | H |
| C$_2$H$_5$ | C$_2$H$_5$ | O | H |
| C$_2$H$_5$ | C$_2$H$_5$ | O | 4-F |
| C$_2$H$_5$ | C$_2$H$_5$ | O | 4-Cl |
| C$_2$H$_5$ | C$_2$H$_5$ | O | 4-CH$_3$ |
| C$_2$H$_5$ | C$_2$H$_5$ | O | 6-F |
| C$_2$H$_5$ | C$_2$H$_5$ | O | 4,6-di-F |
| C$_2$H$_5$ | CH$_2$CH=CH$_2$ | O | H |
| C$_2$H$_5$ | CH$_2$CH=CH$_2$ | O | 4-F |
| C$_2$H$_5$ | CH$_2$CH=CH$_2$ | O | 4-Cl |
| C$_2$H$_5$ | CH$_2$C(CH$_3$)=CH$_2$ | O | H |
| C$_2$H$_5$ | CH$_2$C(CH$_3$)=CH$_2$ | O | 4-F |

TABLE 1-continued

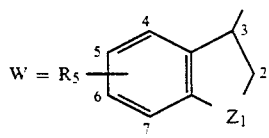

| R₁ | R₂ | Z₁ | R₅ |
|---|---|---|---|
| C₂H₅ | CH₂C(CH₃)=CH₂ | O | 4-CH₃ |
| CH₃ | CH₂C(CH₃)=CH₂ | O | 4-Cl |
| CH₃ | CH₂C(CH₃)=CH₂ | O | 4-F |
| CH₃ | CH₂C(CH₃)=CH₂ | O | H |
| CH₃ | i-C₃H₇ | O | H |
| CH₃ | i-C₃H₇ | O | 4,6-di-F |
| CH₃ | i-C₃H₇ | O | 4-F |
| CH₃ | i-C₃H₇ | O | 4-Cl |
| CH₃ | i-C₃H₇ | O | 4-CH₃ |
| CH₃ | i-C₃H₇ | S | 4-CH₃ |
| CH₃ | i-C₃H₇ | S | 4-F |
| CH₃ | i-C₃H₇ | S | 4-Cl |
| CH₃ | i-C₃H₇ | S | 4,6-di-F |
| CH₃ | i-C₃H₇ | S | H |
| C₂H₅ | C₂H₅ | S | H |
| C₂H₅ | C₂H₅ | S | 4-CH₃ |
| C₂H₅ | C₂H₅ | S | 4-F |
| C₂H₅ | C₂H₅ | S | 4-Cl |
| C₂H₅ | CH₂CH=CH₂ | S | H |
| C₂H₅ | C₂H₅ | NCH₃ | H |
| CH₃ | C₂H₅ | NCH₃ | H |
| CH₃ | i-C₃H₇ | NCH₃ | H |
| C₂H₅ | CH₂CH=CH₂ | NCH₃ | H |

TABLE 2

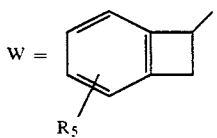

| R₁ | R₂ | R₅ |
|---|---|---|
| CH₃ | CH₃ | H |
| CH₃ | CH₃ | 4-F |
| CH₃ | CH₃ | 4-Cl |
| CH₃ | CH₃ | 4-CH₃ |
| CH₃ | CH₃ | 6-F |
| CH₃ | C₂H₅ | H |
| CH₃ | C₂H₅ | 4-F |
| CH₃ | C₂H₅ | 6-F |
| CH₃ | i-C₃H₇ | H |
| CH₃ | i-C₃H₇ | 4-F |
| CH₃ | i-C₃H₇ | 6-F |
| CH₃ | i-C₃H₇ | 4-Cl |
| CH₃ | i-C₃H₇ | 4-CH₃ |
| CH₃ | i-C₃H₇ | 4-OCH₃ |
| CH₃ | i-C₃H₇ | 4-SCH₃ |
| CH₃ | i-C₃H₇ | 5-CN |
| CH₃ | CCl(CH₃)₂ | H |
| CH₃ | CCl(CH₃)₂ | 4-F |
| CH₃ | C(CH₃)₂SO₂CH₃ | H |
| CH₃ | C(CH₃)₂OCH₃ | H |
| CH₃ | C(CH₃)₂CN | H |
| CH₃ | C(CH₃)₂OH | 4-Br |
| CH₃ | C(CH₃)₂OH | H |
| CH₃ | C(CH₃)₂SO₂Ph | H |
| CH₃ | Ph | H |
| CH₃ | H | H |
| CH₃ | CH₂CO₂CH₃ | H |
| CH₃ | CH₂CO₂H | 4-F |
| CH₃ | CH₂Ph | H |
| CH₃ | CH₂CH=CH₂ | H |
| CH₃ | CH₂CH=CH₂ | 4-F |
| C(CH₃)=CH₂ | | H |
| CH₃ | CH₂C(CH₃)=CH₂ | H |
| CH₃ | CH₂C≡CH | H |
| C₂H₅ | CH₂C≡CH | H |
| C₂H₅ | CH₂CH=CH₂ | 4-F |
| C₂H₅ | CH₂CH=CH₂ | H |

TABLE 2-continued

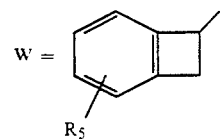

| R₁ | R₂ | R₅ |
|---|---|---|
| C₂H₅ | C₂H₅ | 4-F |
| C₂H₅ | C₂H₅ | 4-Cl |
| C₂H₅ | C₂H₅ | 6-F |
| C₂H₅ | C₂H₅ | 4-CH₃ |
| C₂H₅ | C₂H₅ | H |

TABLE 3

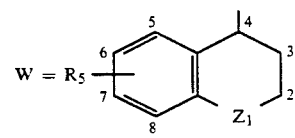

| R₁ | R₂ | Z₁ | R₅ |
|---|---|---|---|
| CH₃ | CH₃ | O | H |
| CH₃ | CH₃ | O | 5-F |
| CH₃ | CH₃ | O | 5-CH₃ |
| CH₃ | i-C₃H₇ | O | 5-CH₃ |
| CH₃ | i-C₃H₇ | O | 5-Cl |
| CH₃ | i-C₃H₇ | O | 5-F |
| CH₃ | i-C₃H₇ | O | H |
| CH₃ | i-C₃H₇ | O | 5,7-di-F |
| CH₃ | C₂H₅ | O | H |
| C₂H₅ | CH₂CH=CH₂ | O | H |
| C₂H₅ | C₂H₅ | O | H |
| C₂H₅ | C₂H₅ | O | 5-F |
| C₂H₅ | C₂H₅ | O | 5-Cl |
| C₂H₅ | C₂H₅ | O | 5-CH₃ |
| C₂H₅ | C₂H₅ | O | 5,7-di-F |
| C₂H₅ | C₂H₅ | CH₂ | 5,7-di-F |
| C₂H₅ | C₂H₅ | CH₂ | 5-F |
| C₂H₅ | C₂H₅ | CH₂ | 5-Cl |
| C₂H₅ | C₂H₅ | CH₂ | 5-CH₃ |
| C₂H₅ | C₂H₅ | CH₂ | H |
| C₂H₅ | CH₂CH=CH₂ | CH₂ | H |
| C₂H₅ | CH₂CH=CH₂ | CH₂ | 5-F |
| CH₃ | CH₂CH=CH₂ | CH₂ | 5-F |
| CH₃ | CH₂CH=CH₂ | CH₂ | H |
| CH₃ | C(CH₃)₂Cl | CH₂ | H |
| CH₃ | C(CH₃)=CH₂ | CH₂ | H |
| CH₃ | i-C₃H₇ | CH₂ | 5-OCH₃ |
| CH₃ | i-C₃H₇ | CH₂ | 5-CN |
| CH₃ | i-C₃H₇ | CH₂ | 5-SCH₃ |
| CH₃ | i-C₃H₇ | CH₂ | H  colorless oil; MS (SP/CI) 153 (9%), 135 (11%), 131 (100%) |
| CH₃ | i-C₃H₇ | CH₂ | 5-Cl |
| CH₃ | i-C₃H₇ | CH₂ | 5-CH₃ |
| CH₃ | i-C₃H₇ | CH₂ | 5-F |
| CH₃ | i-C₃H₇ | CH₂ | 5,7-di-F |
| CH₃ | CH₂CH=CH₂ | CH₂ | H |
| CH₃ | CH₂CH=CH₂ | CH₂ | 5-F |
| CH₃ | CH₂CH=CH₂ | CH₂ | 5-CH₃ |
| CH₃ | CH₂CH=CH₂ | CH₂ | 5-Cl |
| CH₃ | CH₂CH=CH₂ | S | 5-Cl |
| CH₃ | CH₂CH=CH₂ | S | 5-F |
| CH₃ | CH₂CH=CH₂ | S | H |
| C₂H₅ | CH₂CH=CH₂ | S | H |
| C₂H₅ | CH₂CH=CH₂ | S | 5-F |
| C₂H₅ | CH₂CH=CH₂ | S | 5-CH₃ |
| C₂H₅ | C₂H₅ | S | 5-CH₃ |
| C₂H₅ | C₂H₅ | S | 5-F |
| C₂H₅ | C₂H₅ | S | H |
| C₂H₅ | C₂H₅ | S | 5,7-di-F |
| CH₃ | C₂H₅ | S | H |
| CH₃ | i-C₃H₇ | S | H |
| CH₃ | i-C₃H₇ | S | 5-F |
| CH₃ | i-C₃H₇ | S | 5-Cl |

TABLE 3-continued

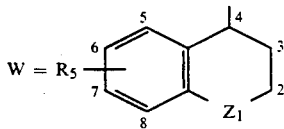

| R₁ | R₂ | Z₁ | R₅ |
|---|---|---|---|
| CH₃ | i-C₃H₇ | S | 5-CH₃ |
| CH₃ | i-C₃H₇ | S | 5,7-di-F |
| CH₃ | i-C₃H₇ | NCH₃ | H |

TABLE 4

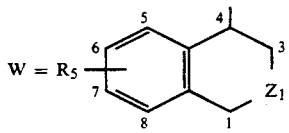

| R₁ | R₂ | Z₁ | R₅ |
|---|---|---|---|
| CH₃ | i-C₃H₇ | S | H |
| CH₃ | i-C₃H₇ | S | 5-F |
| CH₃ | i-C₃H₇ | S | 5-Cl |
| CH₃ | i-C₃H₇ | S | 5-CH₃ |
| CH₃ | i-C₃H₇ | S | 5,7-di-F |
| CH₃ | CH₂CH=CH₂ | S | 5,7-di-F |
| CH₃ | CH₂CH=CH₂ | S | 5-F |
| CH₃ | CH₂CH=CH₂ | S | H |
| C₂H₅ | CH₂CH=CH₂ | S | H |
| C₂H₅ | CH₂CH=CH₂ | S | 5-F |
| C₂H₅ | CH₂CH=CH₂ | S | 5,7-di-F |
| C₂H₅ | C₂H₅ | S | 5,7-di-F |
| C₂H₅ | C₂H₅ | S | H |
| C₂H₅ | C₂H₅ | S | 5-Cl |
| C₂H₅ | C₂H₅ | S | 5-CH₃ |
| C₂H₅ | C₂H₅ | S | 5-F |
| C₂H₅ | C₂H₅ | O | 5-F |
| C₂H₅ | C₂H₅ | O | 5-Cl |
| C₂H₅ | C₂H₅ | O | 5-CH₃ |
| C₂H₅ | C₂H₅ | O | H |
| C₂H₅ | C₂H₅ | O | 5,7-di-F |
| C₂H₅ | CH₂CH=CH₂ | O | H |
| C₂H₅ | CH₂C≡CH | O | H |
| C₂H₅ | CH₂C≡CH | O | 5-F |
| CH₃ | CH₂C≡CH | O | 5-F |
| CH₃ | CH₂C≡CH | O | H |
| CH₃ | i-C₃H₇ | O | H |
| CH₃ | i-C₃H₇ | O | 5-Cl |
| CH₃ | i-C₃H₇ | O | 5-CH₃ |
| CH₃ | i-C₃H₇ | O | 5-F |
| CH₃ | i-C₃H₇ | O | 5,7-di-F |
| CH₃ | i-C₃H₇ | NC₂H₅ | H |
| CH₃ | i-C₃H₇ | NH | H |
| CH₃ | i-C₃H₇ | NCH₃ | H |
| C₂H₅ | C₂H₅ | NCH₃ | H |
| C₂H₅ | CH₂CH=CH₂ | NCH₃ | H |

TABLE 5

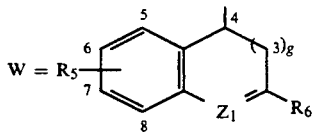

| R₁ | R₂ | Z₁ | g | R₅ | R₆ |
|---|---|---|---|---|---|
| C₂H₅ | C₂H₅ | CH | 0 | H | H |
| C₂H₅ | C₂H₅ | CH | 0 | 5-F | H |
| C₂H₅ | C₂H₅ | CH | 0 | 5,7-di-F | H |
| C₂H₅ | CH₂CH=CH₂ | CH | 0 | 5-CH₃ | H |
| C₂H₅ | CH₂CH=CH₂ | CH | 0 | 5-F | H |
| C₂H₅ | CH₂CH=CH₂ | CH | 0 | H | H |
| CH₃ | CH₂CH=CH₂ | CH | 0 | H | H |

TABLE 5-continued

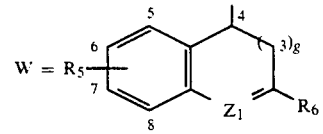

| R₁ | R₂ | Z₁ | g | R₅ | R₆ |
|---|---|---|---|---|---|
| CH₃ | CH₂CH=CH₂ | CH | 0 | 5-F | H |
| CH₃ | i-C₃H₇ | CH | 0 | 5-F | H |
| CH₃ | i-C₃H₇ | CH | 0 | 5,7-di-F | H |
| CH₃ | i-C₃H₇ | CH | 0 | H | H |
| CH₃ | i-C₃H₇ | CH | 1 | H | H |
| CH₃ | CH₂CH=CH₂ | CH | 1 | H | H |
| C₂H₅ | CH₂CH=CH₂ | CH | 1 | H | H |
| C₂H₅ | C₂H₅ | CH | 1 | H | H |
| C₂H₅ | C₂H₅ | N | 1 | H | H |
| C₂H₂ | CH₂CH=CH₂ | N | 1 | H | H |
| CH₃ | CH₂CH=CH₂ | N | 1 | H | H |
| CH₃ | i-C₃H₇ | N | 1 | H | H |
| CH₃ | i-C₃H₇ | N | 1 | H | OCH₃ |

TABLE 6

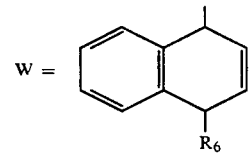

| R₁ | R₂ | R₆ |
|---|---|---|
| C₂H₅ | C₂H₅ | H |
| C₂H₅ | C₂H₅ | OCH₃ |
| C₂H₅ | CH₂CH=CH₂ | OCH₃ |
| C₂H₅ | CH₂CH=CH₂ | H |
| CH₃ | CH₂CH=CH₂ | H |
| CH₃ | CH₂CH=CH₂ | OCH₃ |
| CH₃ | i-C₃H₇ | OCH₃ |
| CH₃ | i-C₃H₇ | H |

TABLE 7

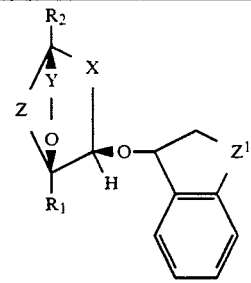

| R₁ | R₂ | X | Y | Z | Z¹ |
|---|---|---|---|---|---|
| CH₃ | H | CH₂ | C(CH₃)₂ | CH₂CH₂ | CH₂ |
| CH₃ | H | CH₂ | C(C₂H₅)₂ | CH₂CH₂ | CH₂ |
| CH₃ | H | CH₂ | C (cyclopentyl) | CH₂CH₂ | CH₂ |
| CH₃ | H | CH₂ | C (cyclohexyl) | CH₂CH₂ | CH₂ |
| C₂H₅ | H | CH₂ | C(C₂H₅)₂ | CH₂CH₂ | CH₂ |
| CH₃ | H | CH₂ | C(CH₃)₂ | CH₂ | CH₂ |
| CH₃ | H | CH₂ | C(C₂H₅)₂ | CH₂ | CH₂ |

TABLE 7-continued

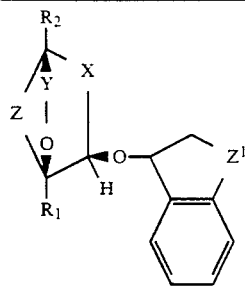

| R₁ | R₂ | X | Y | Z | Z¹ |
|---|---|---|---|---|---|
| $CH_3$ | H | — | $C(CH_3)_2$ | $CH_2CH_2$ | $CH_2$ |
| $CH_3$ | $CH_3$ | $CH_2$ | — | $CH_2CH_2CH_2$ | $CH_2$ |
| $CH_3$ | H | $CH_2CH_2$ | $C(CH_3)_2$ | $CH_2$ | $CH_2$ |
| $CH_3$ | H | $CH_2CH_2$ | $C(C_2H_5)_2$ | $CH_2$ | $CH_2$ |
| $CH_3$ | H | $CH_2CH_2$ | $C(CH_3)_2$ | $CH_2$ | $CH_2$ |
| $C_2H_5$ | H | $CH_2CH_2$ | $C(CH_3)_2$ | $CH_2$ | $CH_2$ |
| $C_2H_5$ | H | $CH_2CH_2$ | $C(C_2H_5)_2$ | $CH_2$ | $CH_2$ |
| $CH_3$ | H | $CH_2CH_2$ | $C(C_2H_5)_2$ | $CH_2$ | $CH_2$ |
| $CH_3$ | H | $CH_2CH_2$ | cyclopentyl | $CH_2$ | $CH_2$ |
| $CH_3$ | H | $CH_2CH_2$ | cyclohexyl | $CH_2$ | $CH_2$ |
| $C_2H_5$ | H | $CH_2CH_2$ | cyclopentyl | $CH_2$ | $CH_2$ |
| $C_2H_5$ | H | $CH_2CH_2$ | cyclohexyl | $CH_2$ | $CH_2$ |
| $CH_3$ | $CH_3$ | $CH_2CH_2$ | — | $CH_2CH_2CH_2$ | $CH_2$ |
| $C_2H_5$ | $C_2H_5$ | $CH_2CH_2$ | — | $CH_2CH_2CH_2$ | $CH_2$ |
| $C_2H_5$ | $CH_2CH=CH_2$ | $CH_2CH_2$ | — | $CH_2CH_2CH_2$ | $CH_2$ |
| $CH_3$ | $CH(CH_3)_2$ | $CH_2CH_2$ | — | $CH_2CH_2CH_2$ | $CH_2$ |
| $CH_3$ | H | $CH_2$ | $C(C_2H_5)_2$ | $CH_2CH_2$ | O |
| $CH_3$ | H | $CH_2$ | $C(C_2H_5)_2$ | $CH_2CH_2$ | O |
| $CH_3$ | H | $CH_2$ | cyclopentyl | $CH_2CH_2$ | O |
| $C_2H_5$ | H | $CH_2$ | cyclohexyl | $CH_2CH_2$ | O |
| $C_2H_5$ | H | $CH_2$ | $C(C_2H_5)_2$ | $CH_2CH_2$ | O |
| $CH_3$ | H | $CH_2$ | $C(CH_3)_2$ | $CH_2$ | O |
| $CH_3$ | H | $CH_2$ | $C(C_2H_5)_2$ | $CH_2$ | O |
| $CH_3$ | H | — | $C(CH_3)_2$ | $CH_2CH_2$ | O |
| $CH_3$ | H | $CH_2CH_2$ | — | $CH_2CH_2CH_2$ | O |
| $CH_3$ | H | $CH_2CH_2$ | $C(CH_3)_2$ | $CH_2$ | O |
| $CH_3$ | H | $CH_2CH_2$ | $C(C_2H_5)_2$ | $CH_2$ | O |
| $C_2H_5$ | H | $CH_2CH_2$ | $C(CH_3)_2$ | $CH_2$ | O |
| $C_2H_5$ | H | $CH_2CH_2$ | $C(CH_3)_2$ | $CH_2$ | O |
| $C_2H_5$ | H | $CH_2CH_2$ | $C(C_2H_5)_2$ | $CH_2$ | O |
| $CH_3$ | H | $CH_2CH_2$ | $C(C_2H_5)_2$ | $CH_2$ | O |

TABLE 7-continued

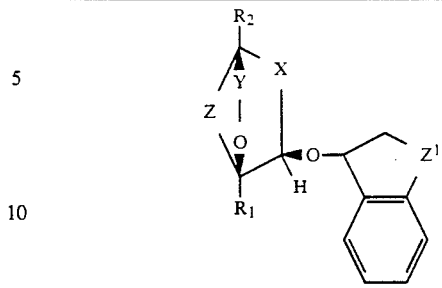

| R₁ | R₂ | X | Y | Z | Z¹ |
|---|---|---|---|---|---|
| $CH_3$ | H | $CH_2CH_2$ | cyclopentyl | $CH_2$ | O |
| $CH_3$ | H | $CH_2CH_2$ | cyclohexyl | $CH_2$ | O |
| $C_2H_5$ | H | $CH_2CH_2$ | cyclopentyl | $CH_2$ | O |
| $C_2H_5$ | H | $CH_2CH_2$ | cyclohexyl | $CH_2$ | O |
| $CH_3$ | $CH_3$ | $CH_2CH_2$ | — | $CH_2CH_2CH_2$ | O |
| $C_2H_5$ | $C_2H_5$ | $CH_2CH_2$ | — | $CH_2CH_2CH_2$ | O |
| $C_2H_5$ | $CH_2CH=CH_2$ | $CH_2CH_2$ | — | $CH_2CH_2CH_2$ | O |

TABLE 8

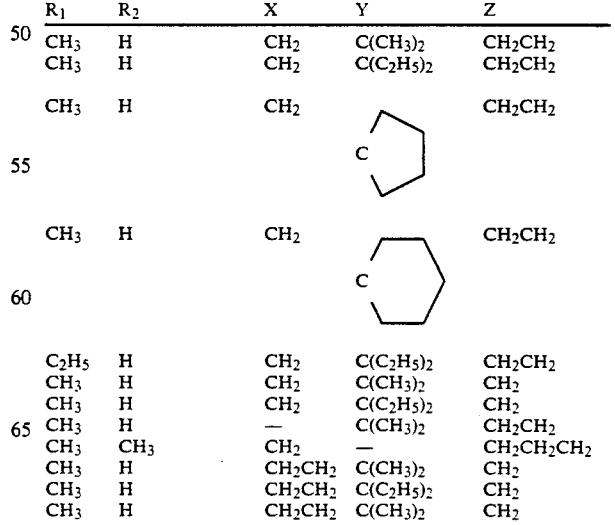

| R₁ | R₂ | X | Y | Z |
|---|---|---|---|---|
| $CH_3$ | H | $CH_2$ | $C(CH_3)_2$ | $CH_2CH_2$ |
| $CH_3$ | H | $CH_2$ | $C(C_2H_5)_2$ | $CH_2CH_2$ |
| $CH_3$ | H | $CH_2$ | cyclopentyl | $CH_2CH_2$ |
| $CH_3$ | H | $CH_2$ | cyclohexyl | $CH_2CH_2$ |
| $C_2H_5$ | H | $CH_2$ | $C(C_2H_5)_2$ | $CH_2CH_2$ |
| $CH_3$ | H | $CH_2$ | $C(CH_3)_2$ | $CH_2$ |
| $CH_3$ | H | $CH_2$ | $C(C_2H_5)_2$ | $CH_2$ |
| $CH_3$ | H | — | $C(CH_3)_2$ | $CH_2CH_2$ |
| $CH_3$ | $CH_3$ | $CH_2$ | — | $CH_2CH_2CH_2$ |
| $CH_3$ | H | $CH_2CH_2$ | $C(CH_3)_2$ | $CH_2$ |
| $CH_3$ | H | $CH_2CH_2$ | $C(C_2H_5)_2$ | $CH_2$ |
| $CH_3$ | H | $CH_2CH_2$ | $C(CH_3)_2$ | $CH_2$ |

TABLE 8-continued

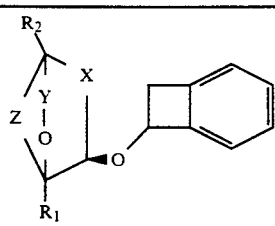

| R₁ | R₂ | X | Y | Z |
|---|---|---|---|---|
| C₂H₅ | H | CH₂CH₂ | C(CH₃)₂ | CH₂ |
| C₂H₅ | H | CH₂CH₂ | C(CH₂CH₃) | CH₂ |
| CH₃ | H | CH₂CH₂ | C(C₂H₅)₂ | CH₂ |
| CH₃ | H | CH₂CH₂ | cyclopentyl | CH₂ |
| CH₃ | H | CH₂CH₂ | cyclohexyl | CH₂ |

TABLE 8-continued

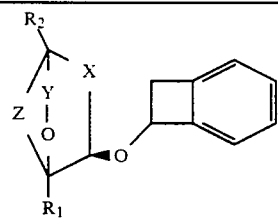

| R₁ | R₂ | X | Y | Z |
|---|---|---|---|---|
| C₂H₅ | H | CH₂CH₂ | cyclopentyl | CH₂ |
| C₂H₅ | H | CH₂CH₂ | cyclohexyl | CH₂ |
| CH₃ | CH₃ | CH₂CH₂ | — | CH₂CH₂CH₂ |
| C₂H₅ | C₂H₅ | CH₂CH₂ | — | CH₂CH₂CH₂ |
| C₂H₅ | CH₂CH=CH₂ | CH₂CH₂ | — | CH₂CH₂CH₂ |

TABLE 9

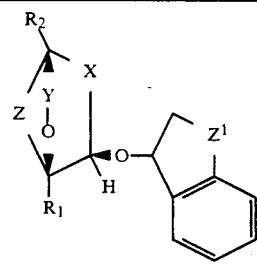

| R₁ | R₂ | X | Y | Z | Z¹ |
|---|---|---|---|---|---|
| CH₃ | H | CH₂ | C(CH₃)₂ | CH₂CH₂ | CH₂CH₂ |
| CH₃ | H | CH₂ | C(C₂H₅)₂ | CH₂CH₂ | CH₂CH₂ |
| CH₃ | H | CH₂ | cyclopentyl | CH₂CH₂ | CH₂CH₂ |
| CH₃ | H | CH₂ | cyclohexyl | CH₂CH₂ | CH₂CH₂ |
| C₂H₅ | H | CH₂ | C(C₂H₅)₂ | CH₂CH₂ | CH₂CH₂ |
| CH₃ | H | CH₂ | C(CH₃)₂ | CH₂ | CH₂CH₂ |
| CH₃ | H | CH₂ | C(C₂H₅)₂ | CH₂ | CH₂CH₂ |
| CH₃ | H | — | C(CH₃)₂ | CH₂CH₂ | CH₂CH₂ |
| CH₃ | CH₃ | CH₂ | — | CH₂CH₂CH₂ | CH₂CH₂ |
| CH₃ | H | CH₂CH₂ | C(CH₃)₂ | CH₂ | CH₂CH₂ |
| CH₃ | H | CH₂CH₂ | C(C₂H₅)₂ | CH₂ | CH₂CH₂ |
| CH₃ | H | CH₂CH₂ | C(CH₃)₂ | CH₂ | CH₂CH₂ |
| C₂H₅ | H | CH₂CH₂ | C(CH₃)₂ | CH₂ | CH₂CH₂ |
| C₂H₅ | H | CH₂CH₂ | C(C₂H₅)₂ | CH₂ | CH₂CH₂ |
| CH₃ | H | CH₂CH₂ | C(C₂H₅)₂ | CH₂ | CH₂CH₂ |
| CH₃ | H | CH₂CH₂ | cyclopentyl | CH₂ | CH₂CH₂ |

TABLE 9-continued

| R₁ | R₂ | X | Y | Z | Z¹ |
|---|---|---|---|---|---|
| CH₃ | H | CH₂CH₂ | cyclopentyl (C) | CH₂ | CH₂CH₂ |
| C₂H₅ | H | CH₂CH₂ | cyclopentyl (C) | CH₂ | CH₂CH₂ |
| C₂H₅ | H | CH₂CH₂ | cyclohexyl (C) | CH₂ | CH₂CH₂ |
| CH₃ | CH₃ | CH₂CH₂ | — | CH₂CH₂CH₂ | CH₂CH₂ |
| C₂H₅ | C₂H₅ | CH₂CH₂ | — | CH₂CH₂CH₂ | CH₂CH₂ |
| C₂H₅ | CH₂CH=CH₂ | CH₂CH₂ | — | CH₂CH₂CH₂ | CH₂CH₂ |
| CH₃ | H | CH₂ | cyclopentyl (C) | CH₂CH₂ | CH₂O |
| C₂H₅ | H | CH₂ | cyclohexyl (C) | CH₂CH₂ | CH₂O |
| C₂H₅ | H | CH₂ | C(C₂H₅)₂ | CH₂CH₂ | CH₂O |
| CH₃ | H | CH₂ | C(CH₃)₂ | CH₂ | CH₂O |
| CH₃ | H | CH₂ | C(C₂H₅)₂ | CH₂ | CH₂O |
| CH₃ | H | — | C(CH₃)₂ | CH₂CH₂ | CH₂O |
| CH₃ | H | CH₂CH₂ | — | CH₂CH₂CH₂ | CH₂O |
| CH₃ | H | CH₂CH₂ | C(CH₃)₂ | CH₂ | CH₂O |
| CH₃ | H | CH₂CH₂ | C(C₂H₅)₂ | CH₂ | CH₂O |
| CH₃ | H | CH₂CH₂ | C(CH₃)₂ | CH₂ | CH₂O |
| C₂H₅ | H | CH₂CH₂ | C(CH₃)₂ | CH₂ | CH₂O |
| C₂H₅ | H | CH₂CH₂ | C(CH₃)₂ | CH₂ | CH₂O |
| C₂H₅ | H | CH₂CH₂ | C(C₂H₅)₂ | CH₂ | CH₂O |
| CH₃ | H | CH₂CH₂ | C(C₂H₅)₂ | CH₂ | CH₂O |
| CH₃ | H | CH₂CH₂ | cyclopentyl (C) | CH₂ | CH₂O |
| CH₃ | H | CH₂CH₂ | cyclohexyl (C) | CH₂ | CH₂O |
| C₂H₅ | H | CH₂CH₂ | cyclopentyl (C) | CH₂ | CH₂O |

TABLE 9-continued

| $R_1$ | $R_2$ | X | Y | Z | $Z^1$ |
|---|---|---|---|---|---|
| $C_2H_5$ | H | $CH_2CH_2$ | ‐C₅H₁₀‐ (cyclohexylidene) | $CH_2$ | $CH_2O$ |
| $CH_3$ | $CH_3$ | $CH_2CH_2$ | — | $CH_2CH_2CH_2$ | $CH_2O$ |
| $C_2H_5$ | $C_2H_5$ | $CH_2CH_2$ | — | $CH_2CH_2CH_2$ | $CH_2O$ |
| $C_2H_5$ | $CH_2CH=CH_2$ | $CH_2CH_2$ | — | $CH_2CH_2CH_2$ | $CH_2O$ |

FORMULATIONS

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE 9

| | Active Ingredient | Weight Percent* Diluent(s) | Surfactant(s) |
|---|---|---|---|
| Wettable Powders | 5–60 | 39–94 | 1–10 |
| Emulsifiable Concentrates | 3–80 | 20–95 | 0–20 |
| Dusts | 1–25 | 70–99 | 0–5 |
| Granules and Pellets | 0.1–50 | 50–99.9 | 0–15 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, Jun. 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE A

Wettable Powder

| | |
|---|---|
| 7-oxabicyclo((2.2.1))heptane' 2-(2,3-dihydro-1H-inden-1-yloxy)-1-methyl-4-(1-methylethyl) | 60% |
| sodium alkylnaphthalenesulfonate | 2% |
| sodium ligninsulfonate | 2% |

| synthetic amorphous silica | 36% |

The active ingredient is first sprayed onto the amorphous silica, then the ingredients are blended, hammer-milled until all the solids are essentially under 50 microns, reblended, and packaged.

EXAMPLE B

Wettable Powder

| | |
|---|---|
| 7-oxabicyclo((2.2.1))heptane' 2-(2,3-dihydro-1H-inden-1-yloxy)-1-methyl-4-(1-methylethyl) | 50% |
| sodium alkylnaphthalenesulfonate | 2% |
| low viscosity methyl cellulose | 2% |
| diatomaceous earth | 46% |

The active ingredient is first sprayed onto the diatomaceous earth then the ingredients are blended, coarsely hammer-milled and then air-milled to produce particles essentially all below 10 microns in diameter. The product is reblended before packaging.

EXAMPLE C

Granule

| | |
|---|---|
| Wettable Powder of Example 4 | 5% |
| attapulgite granules (U.S.S. 20–40 mesh; 0.84–0.42 mm) | 95% |

A slurry of wettable powder containing 25% solids is sprayed on the surface of attapulgite granules in a double-cone blender. The granules are dried and packaged.

EXAMPLE D

Emulsifiable Concentrate

| | |
|---|---|
| 7-oxabicyclo((2.2.1))heptane' 2-(2,3-dihydro-1H-inden-1-yloxy)-1-methyl-4-(1-methylethyl) | 40% |
| Atlox 3403F | 3% |
| Atlox 3404F | 3% |
| xylene | 54% |

The active ingredient and Atlox emulsifiers are dissolved in the solvent, filtered and packaged. Atlox 3403F and 3404F are blends of anionic and ionic emulsifiers from ICI Americas, Inc.

EXAMPLE E

Low Strength Granule

| | |
|---|---|
| 7-oxabicyclo((2.2.1))heptane' 2-(2,3-dihydro-1H-inden-1-yloxy)-1-methyl-4-(1-methylethyl) | 5% |
| atapulgite granules (U.S.S. 20–40 mesh) | 95% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE F

Granule

| | |
|---|---|
| 7-oxabicyclo((2.2.1))heptane' 2-(2,3-dihydro-1H-inden-1-yloxy)-1-methyl-4-(1-methylethyl) | 50% |
| wetting agent | 1% |
| crude ligninsulfonate salt (containing 5–20% of the natural sugars) | 10% |
| attapulgite clay | 39% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE G

Concentrated Emulsion

| | |
|---|---|
| 7-oxabicyclo((2.2.1))heptane' 2-(2,3-dihydro-1H-inden-1-yloxy)-1-methyl-4-(1-methylethyl) | 25% |
| xylene | 25% |
| Atlox 3404F | 5% |
| G1284 | 5% |
| ethylene glycol | 8% |
| water | 32% |

The active ingredient, solvent and emulsifiers are blended together. This solution is added to a mixture of the ethylene glycol and water with stirring.

EXAMPLE H

Solution

| | |
|---|---|
| 7-oxabicyclo((2.2.1))heptane' 2-(2,3-dihydro-1H-inden-1-yloxy)-1-methyl-4-(1-methylethyl) | 5% |
| water | 95% |

The compound is added directly to the water with stirring to produce the solution, which may then be packaged for use.

EXAMPLE I

Dust

| | |
|---|---|
| 7-oxabicyclo((2.2.1))heptane' 2-(2,3-dihydro-1H-inden-1-yloxy)-1-methyl-4-(1-methylethyl) | 10% |
| attapulgite | 10% |
| Pyrophyllite | 80% |

The active ingredient is sprayed onto the attapulgite and then passed through a hammer-mill to produce particles substantially all below 200 microns. The ground concentrate is then blended with powdered pyrophyllite until homogeneous.

UTILITY

Test results indicate that compounds of this invention are highly active preemergent and/or postemergent herbicides or plant growth regulators. These compounds are useful for postemergence grass control in agronomic crops and are particularly useful for preemergence broad-spectrum grass and selected small-seeded broadleaf weed control in agronomic crops. Agronomic crops such as barley (*Hordeum vulgare*), corn (*Zea mays*), cotton (*Gossypium hirsutum*), rape (*Brassica napus*), rice (*Oryza sativa*), sorghum (*Sorghum bicolor*), soybean (*Glycine max*), sugar beet (*Beta vulgaris*), and wheat (*Triticum aestivum*) show little or no injury when treated with application rates necessary for weed control for many of the compounds in this invention. Many of the compounds of this invention are also particularly suitable for barnyardgrass (*Echinochloa crus-galli*) control in transplanted rice. Troublesome weed species that are suppressed or controlled are grass weeds such as barnyardgrass (*Echinochloa crus-galli*), blackgrass (*Alopecurus myosuroides*), cheatgrass (*Bromus secalinus*), crabgrass (Digitaria spp.), downy brome (*Bromus tectorum*), foxtail (Setaria spp.), johnsongrass (*Sorghum halepense*), and wild oat (*Avena fatua*); broadleaf weeds such as lambsquarters (*Chenopodium album*) and velvetleaf (*Abutilon theophrasti*); and sedge (*Cyperus* spp.).

Test results also indicate that compounds of this invention have utility for broad-spectrum pre-and/or postemergence weed control in other areas where control of vegetation is desired, such as around storage tanks, parking lots, drive-in theaters, billboards, highways, and railroad structures and in fallow areas of crop production such as in wheat, barley, and in plantation crops such as palm, pineapple, plantin, banana, citrus, rubber, sugarcane, etc.

Rates of application for compounds of this invention are determined by a number of factors. These factors include: formulation selected, method of application, amount of vegetation present, growing conditions, etc. In general terms, the subject compounds should be applied at rates from 0.01 to 20 kg/ha with a preferred rate range of from 0.05 to 1 kg/ha. One skilled in the art can easily determine rates needed for the desired level of weed control.

Compounds of this invention may be used alone or in combination with other commercial herbicides, insecticides, or fungicides. The following list exemplifies some of the herbicides suitable for use in mixtures. A combination of a compound from this invention with one or more of the following herbicides may be particularly useful for weed control.

| Common Name | Chemical Name |
| --- | --- |
| acetochlor | 2-chloro-B-(ethoxymethyl)-N-(2-ethyl-6-methylphenyl)acetamide |
| acifluorfen | 5-[2-chloro-4-(trifluoromethyl)phenoxy]-2-nitrobenzoic acid |
| acrolein | 2-propenal |
| alachlor | 2-chloro-2,6-diethylphenyl-N-(methoxy methyl)acetanilide |
| ametryn | N-ethyl-N'-1(1-methylethyl)-6-(methylthio)-1,3,5-triazine-2,4-diamine |
| amitrole | 1H-1,2,4-triazol-3-amine |
| AMS | ammonium sulfamate |
| asulam | methyl [(4-aminophenyl)sulfonyl]carbamate |
| atrazine | 6-chloro-N-ethyl-N'-(1methylethyl)-1,3,5-triazine-2,4-diamine |
| barban | 4-chloro-2-butynyl 3-chlorophenylcarbamate |
| benefin | N-butyl-N-ethyl-2,6-dinitro-4-(trifluoromethyl)benzenamine |
| bensulfuron methyl | 2-[[[[(4,6-dimethoxy-2-pyrimidinyl)-amino]carbonyl]amino]sulfonyl]methyl]-benzoic acid, methyl ester |
| bensulide | O,O-bis(1-methylethyl)S-[2-[(phenylsulfonyl)-amino]ethyl]phosphorodithioate |
| bentazon | 3-(1-methylethyl)-(1H)-2,2,3-benzothiadiazinO 4(3H)-one 2,2-dioxide |
| benzofluor | N-[4-(ethylthio)-2-(trifluoromethyl)phenyl]-methanesulfonamide |
| benzoylprop | N-benzoyl-N-(3,4-dichlorophenyl)-DL-alaine |
| bifenox | methyl 5-(2,4-dichlorophenoxy)-2-nitrobenzoate |
| bromacil | 5-bromo-6-methyl-3-(1-methylpropyl)-2,4-(1H,3H)pyrimidinedione |
| bromoxynil | 3,5-dibromo-4-hydroxybenzonitrile |
| butachlor | N-(butoxymethyl)-2-chloro-N-(2,6-diethylphenyl)acetamide |
| buthidazole | 3-[5-(1,1-dimethylethyl)-1,3,4-thiadiazol-2-yl]-4-hydroxy-1-methyl-2-imidazolidinone |
| butralin | 4-(1,1-dimethylethyl)-N-(1-methylpropyl)-2,6-dinitrobenzenamine |
| butylate | S-ethyl-bis(2-methylpropyl)carbamothioate |
| cacodylic acid | dimethyl arsinic acid |
| CDAA | 2-chloro-N,N-di-2-propenylacetamide |
| CDEC | 2-chloroallyl diethyldithiocarbamate |
| chloramben | 3-amino-2,5-dichlorobenzoic acid |
| chlorbromuron | 3-(4-bromo-3-chlorophenyl)-1-methoxy-1-methylurea |
| chlorimuron ethyl | 2-[[[[(4-chloro-6-methoxy-2-pyrimidinyl)-amino]carbonyl]amino]sulfonyl]benzoic-acid, ethyl ester |
| chloroxuron | N'-[4-(4-chlorophenoxy)phenyl]-N,N-dimethylurea |
| chlorpropham | 1-methylethyl 3-chlorophenylcarbamate |
| chlorsulfuron | 2-chloro-N-[(4-methoxy-6-methyl-1,3,5-triazin-2-yl)amino]carbonyl]benzenesulfonamide |
| chlortoluron | N'-(3-chloro-4-methylphenyl-N,N-dimethylurea |
| cinmethylin | exo-1-methyl-4-(1-methylethyl)-2-[(2-methylphenyl)methoxy]-7-oxabicyclo[2.2.1]heptane |
| clethodim | (E,E)-(%)-2-[[(3-chloro-2-prophenyl)oxy]-imino]propyl]-5-[2-(ethylthio)-propyl]-3-hydroxy-2-cyclohexan-1-one |
| clomazone | 2-[(2-chlorophenyl(methyl]-4,4-dimethyl-3-isoxazolidinone |
| cloproxydim | (E,E)-2-[1-[[(3-chloro-2-propenyl)oxy) imino[butyl]-5-[2-(ethylthio)propyl]-3-hydroxy-2-cyclohexen-1-one |
| clopyralid | 3,6-dichloro-2-pyridinecarboxylic acid |
| CMA | calcium salt of MAA |
| cyanazine | 2-[[4-chloro-6-(ethylamino)-1,3,5-triazin-2-yl]amino]-2-methyl-propanenitrile |
| cycloate | S-ethyl cyclohexylethylcarbamothioate |
| cycluron | 3-cyclooctyl-1,1-dimethylurea |
| cyperquat | 1-methyl-4-phenylpyridinium |
| cyprazine | 2-chloro-4-(cyclopropylamino)-6-(iso- |
| cypromid | 3',4'-dichlorocyclopropanecarboxanilide |
| dalapon | 2,2-dichloropropionic acid |
| dalapon | 2,2-dichloropropanoic acid |
| dazomet | tetrahydro-3,5-dimethyl-2H-1,3,5-thiadiazine-2-thione |
| DCPA | dimethyl 2,3,5,6-tetrachloro-1,4-benzenedicarboxylate |
| desmediphan | ethyldesmetryn[3-[[(phenylamino)-carbonyl]oxy]phenyl]carbamate |
| desmetryn | 2-(isopropylamino)-4-(methylamino)-6- |
| diallate | S-(2,3-dichloro-2-propenyl) bis(1-methylethyl)carbamothioate |
| dicamba | 3,6-dichloro-2-methoxybenzoic acid |
| dichlobenil | 2,6-dichlorobenzonitrile |
| dichlorprop | (%)-2-(2,4-dichlorophenoxy)propanoic acid |
| diclofop | (%)-2-[4-(2,4-dichlorophenoxy)phenoxy] - propanoic acid |
| diethatyl | N-(chloroacetyl)-N-(2,6-diethylphenyl)-glycine |
| difenzoquat | 1,2-dimethyl-3,5-diphenyl-1H-pyrazolium |
| dinitramine | $N^3,N^3$-diethyl-2,4-dinitro-6-(trifluoromethyl)-1,3-benzenediamine |
| dinoseb | 2-(1-methylpropyl)-4,6-dinitrophenol |

| Common Name | Chemical Name |
|---|---|
| diphenamide | N,N-dimethyl-a-phenylbenzeneacetamide |
| dipropetryn | 6-(ethylthio)-N,N'-bis (1-methylethyl)-1,3,5-triazine-2,4-diamine |
| diquat | 6,7-dihydrodipyrido[1,2-a:2',1'-c]-pyrazinediium ion |
| diuron | N'-(3,4-dichlorophenyl)-N,N-dimethylurea |
| DNOC | 2-methyl-4,6-dinitrophenol |
| DPX-M6316 | 3-DSMA[[[[(4-methoxy-6-methyl-1,3,5-triazin-2-yl)amino]carbonyl]amino]-sulfonyl]-2-thiophenecarboxylic acid, methyl ester |
| DPX-V9360 | 2-[[[[(4,6-dimethoxypyrimidin-2-yl)-amino]carbonyl]amino]sulfonyl]-3-pyridinecarboxylic acid, N,N-dimethylamide |
| DSMA | disodium salt of MAA |
| endothall | 7-oxabicyclo[2.2.1]heptane-2,3-dicarboxylic acid |
| EPTC | S-ethyl diproprylcarbamothioate |
| ethafluralin | N-ethyl-N-(2-methyl-2-propenyl)-2,6-dinitro-4-(trifluoromethyl)benzenamine |
| ethofumesate | (±)-2-ethoxy-2,3-dihydro-3,3-dimethyl-5-benzofuranyl methanesulfonate |
| Express* | 2[[[[N-(4-methoxy-6-methyl-1,3,5-triazine-2-yl)-N-methylamino]-carbonyl]amino]sulfonyl]benzoic acid, methyl ester |
| fenac | 2,3,6-trichlorophenylacetic acid |
| fenoxaprop ethyl | (%)-2-[4-[6-chloro-2-benzoxazolyl-oxy]phenoxy]propanoic acid |
| fenuron | N,N-dimethyl-N'-phenylurea |
| fenuron TCA | Salt of fenuron and TCA |
| flamprop | N-benzoyl-N-(3-chloro-4-fluorophenyl)-DL-alanine |
| fluazifop | (%)2-[4-[[5-(trifluoromethyl)-2-pyridinyl]oxy]phenoxy]propanoic acid |
| fluazifop-P | (R)-2-[4-[[5-(trifluoromethyl)-2-pryidinyl]oxy]phenoxy]propanoic acid |
| fluchloralin | N-(2-chloroethyl)-2,6-dinitro-N-propyl-4-(trifluoromethyl)benzenamine |
| fluometuron | N,N-dimethyl-N'-[3-trifluoromethyl) phenyl]urea |
| fluoro-chloridone | 3-chloro-4-(chloromethyl)-1-[3-(trifluoromethyl)phenyl]-2-pyrrolidinone |
| fluorodifen | p-nitrophenyl a,a,a-trifluoro-2-nitro-p-tolyl ether |
| fluorogly-cofen | carboxymethyl 5-[2-chloro-4-(trifluoromethyl)phenoxy]-2-nitrobenzoate |
| fluridone | 1-methyl-3-phenyl-5-[3-(trifluoromethyl)phenyl]-4(1H)-pyridinone |
| fomesafen | 5-[2-chloro-4-trifluoromethyl)phenoxy]-N-(methylsulfonyl)-2-nitrobenzamide |
| fosamine | ethyl hydrogen (aminocarbonyl)phosphate |
| glyphosate | N-(phosphonomethyl)glycine |
| halozyfop | 2-[4-[[3-chloro-5-(trifluoromethyl)-2-pyridinyl]oxy]phenoxy]propanoic acid |
| hexaflurate | potassium hexafluoroarsenate |
| hexazinone | 3-cyclohexyl-6-(dmethylamino)-1-methyl-1,3,5-triazine-2,4(1H,3H)-dione |
| imazametha-benz | 6-(4-isopropyl-4-methyl-5-oxo-2-imadazolin-2-yl)-m-toluic acid, methyl ester |
| imazapyr | (%)-[4,5-dihydro-4-methyl-4-(1-methylethyl)-5-oxo-1H-imidazol-2-yl]-3-pyridinecarboxylic acid |
| imazaquin | 2-[4,5-dihydro-4-methyl-4-(1-methylethyl)-5-oxo-1H-imidazol-2-yl]-3-quinolinecarboxylic acid |
| imazethapyr | (%)-2-[4,5-dihydro-4-methyl-4-(1-methylethyl)-5-oxo-1H-imidazol-2-yl]-5-ethyl-3-pyridinecarboxylic acid |
| ioxynil | 4-hydroxy-3,5-diiodobenzonitrile |
| isopropalin | 4-(1-methylethyl)-2,6-dinitro-N,N-dipropylbenzenamine |
| isoprotoron | N-(4-isopropylphenyl)-N',N'-dimethylurea |
| isouron | N'-[(1,1-dimethylethyl)-3-isoxazolyl]-N,N-dimethylurea |
| isoxaben | N-[3-(1-ethyl-1-methylpropyl)-5-isoxazolyl]-2,6-dimethoxybenzamide |
| karbutilate | 3-[[(dimethylamino)carbonyl]amino]-phenyl (1,1-dimethylethyl)-carbamate |
| lactofen | (%)-2-ethoxy-1-methyl-2-oxoethyl 5-[2-chloro-4-(trifluoromethyl)phenoxy]-2-nitrobenzoate |
| lenacil | 3-cyclohexyl-6,7-dihydro-1H-cyclopenta-pyrimidine-2,4(3H,5H)-dione |
| linuron | N'-(3,4-dichlorophenyl)-N-methoxy-N-methylurea |
| MAA | methylarsonic acid |
| MAMA | monoammonium salt of MAA |
| MCPA | (4-chloro-2-methylphenoxy)acetic acid |
| MCPB | 4-(4-chloro-2-methylphenoxy)butanoic acid |
| mecoprop | (%)-2-(4-chloro-2-methylphenoxy)-propanoic acid |
| mefluidide | N-[2,4-dimethyl-5-[[(trifluoromethyl)-sulfonyl]amino]phenyl]acetamide |
| methal-propalin | N-(2-methyl-2-propenyl)-2,6-dinitro-N-propyl-4-(trifluoromethyl)benzenamide |
| methabenz-thiazuron | 1,3-dimethyl-3-(2-benzothiazolyl)urea |
| metham | methylcarbamodithioic acid |
| methazole | 2-(3,4-dichlorophenyl)-4-methyl-1,2,4-oxadiazolidine-3,5-dione |
| methoxuron | N'-(3-chloro-4-methoxyphenyl)N,N-dimethylurea |
| metolachlor | 2-chloro-N-(2-ethyl-6-methylphenyl)-N-(2-methoxy-1-methylethyl)acetamide |
| metribuzin | 4-amino-6-(1,1-dimetylethyl)-3-(methyl-thio)-1,2,4-triazin-5(4H)-one |
| metsulfuron | 2-[[[[(4-methoxy-6-methyl-1,3,5-triazin-2-yl)amino]carbonyl]amino]-sulfonyl]benzoic acid, methyl ester |
| MH | 1,2-dihydro-3,6-pyridazinedione |
| molinate | S-ethyl hexahydro-1H-azepine-1-carbo-thioate |
| monolinuron | 3-(p-chlorophenyl)-1-methoxy-1-methyl-urea |
| monuron | N'-(4-chlorophenyl)-N,N-dimethylurea |
| monuron TCA | salt of monuron and TCA |
| MSMA | monosodium salt of MAA |
| napropamide | N,N-diethyl-2-(1-naphthalenyloxy)-propanamide |
| naptalam | 2-[(1-naphthalenylamino)carbonyl]-benzoic acid |
| neburon | 1-butyl-3-(3,4-dichlorphenyl)-1-methyl-urea |
| nitralin | 4-(methylsulfonyl)-2,6-dinitro-N,N-dipropylaniline |
| nitrofen | 2,4-dichloro-1-(4-nitrophenoxy)benzene |
| nitrofluorfen | 2-chloro-1-(4-nitrophenoxy)-4-(trifluoromethyl)benzene |
| norea | N,N-dimethyl-N'-(octahydro-4,7-methano-1H-inden-5-yl)urea 3aa,4a,5a,7a,7aa-isomer |
| norflurazon | 4-chloro-5-(methylamino)-2-(3-(tri-fluoromethyl)phenyl]-3(2H)-pyridaz-inone |
| oryzalin | 4-(dipropylamino)-3,5-dinitrobenzene-sulfonamide |
| oxadiazon | 3-[2,4-dichloro-5-(1-methylethoxy)-phenyl]-5-(1,1-dimethylethyl-1,3,4-oxadiazol-2-(3H)-one |
| oxyfluorfen | 2-chloro-1-(3-ethoxy-4-nitrophenoxy)-4-(trifluoromethyl)benzene |
| paraquat | 1,1'-dimethyl-4,4'-dipyridinium ion |
| pebulate | S-propyl butylethylcarbamothioate |
| pendimethalin | N-(1-ethylpropyl)-3,4-dimethyl-2,6-dinitrobenzenamine |
| perfluidone | 1,1,1-trifluoro-N-[2-methyl-4-(phenyl-sulfonyl)phenyl]methanesulfonamide |
| phenmedipham | 3-[(methoxycarbonyl)amino]phenyl-(3-methylphenyl)carbamate |
| picloram | 4-amino-3,5,6-trichloro-2-pyridine-carboxylic acid |

27
-continued

| Common Name | Chemical Name |
|---|---|
| PPG-1013 | 5-(2-chloro-4-(trifluoromethyl)phenoxy)-2-nitroacetophenone oxime-O-acetic acid, methyl ester |
| procyazine | 2-[[4-chloro-6-(cyclopropylamino)-1,3,5-triazine-2-yl]amino]-2-methylpropanenitrile |
| profluralin | N-(cyclopropylmethyl)-2,6-dinitro-N-propyl-4-(trifluoromethyl)benzenamine |
| prometon | 6-methoxy-N,N'-bis(1-methylethyl)-1,3,5-triazine-2,4-diamine |
| prometryn | N,N'-bis(1-methylethyl)-6-(methylthio)-1,3,5-triazine-1,4-diamine |
| pronamide | 3,5-dichloro N-(1,1-dimethyl-2-propynyl)benzamide |
| propachlor | 2-chloro-N-(1-methylethyl-N-phenylacetamide |
| propanil | N-(3,4-dichlorophenyl)propanamide |
| propazine | 6-chloro-N,N'-bis(1-methylethyl)-1,3,5-triazine-2,4-diamine |
| propham | 1-methylethyl phenylcarbamate |
| prosulfalin | N-[[4-(dipropylamino)-3,5-dinitrophenyl]sulfonyl]-S,S-dimethylsulfilimine |
| prynachlor | 2-chloro-N-(1-methyl-2-propynyl)acetanilide |
| pyrazon | 5-amino-3-chloro-2-phenyl-3(2H)-pyridazinone |
| quizalofop | (%)-2-[4[(6-chloro-2-quinoxalinyl)]-oxy]phenoxy]propanoic acid |
| secbumeton | N-ethyl-6-methoxy-N'(1-methylpropyl)-1,3,5-triazine-2,4-diamine |
| sethoxydim | 2-[1-(ethoxyimino)butyl]-5-[2-(ethylthio)propyl]-3-hydroxy-2-cyclohexene-1-one |
| siduron | N-(2-methylcyclohexyl)-N'-phenylurea |
| simazine | 6-chloro-N,N'-diethyl-1,3,5-triazine-2,4-diamine |
| sulfometuron | 2-[[[[(4,6-dimethyl-2-pyrimidinyl)-amino]carbonyl]amino]sulfonyl]-benzoic acid, methyl ester |
| TCA | trichloroacetic acid |
| tebuthiuron | N-[5-(1,1-dimethylethyl)-1,3,4-thiadiazol-2-yl]-N,N'-dimethylurea |
| terbacil | 5-chloro-3(1,1-dimethylethyl)-6-methyl-2,4(1H,3H)-pyrimidinedione |
| terbuchlor | N-(butoxymethyl)-2-chloro-N-[2-1,1-dimethylethyl)-6-methylphenyl]-acetamide |
| terbuthylazine | 2-(tert-butylamino)-4-chloro-6-ethylamino)-s-triazine |
| terbutol | 2,6-di-tert-butyl-p-tolyl methylcarbamate |
| terbutryn | N-(1,1-dimethylethyl)-N'-ethyl-6-methylthio)-2,3,5-triazine-2,4- |
| thiameturon methyl | 3-[[[[(4-methoxy-6-methyl-1,3,5-triazin-2-yl)amino]carbonyl]amino]-sulfonyl]2-thiophenecarboxylic acid, methyl ester |
| thiobencarb | S-[(4-chlorophenyl)methyl]diethylcarbamothioate |
| triallate | S-(2,3,3-trichloro-2-propenyl)bis(1-methylethyl)carbamothioate |
| triclopyr | [(3,5,6-trichloro-2-pyridinyl)-oxy]acetic acid |
| tridiphane | 2-(3,5-dichlorophenyl)-2-(2,2,2-trichloroethyl)oxirane |
| trifluralin | 2,6-dinitro-N,N-dipropyl-4-(trifluoromethyl)benzenamine |
| trimeturon | 1-(p-chlorophenyl)-2,3,3-trimethylpseudourea |
| 2,4- | (2,4-dichlorophenoxy)acetic acid |
| 2,4-B | 4-(2,4-dichlorophenoxy)butanoic acid |
| vernolate | S-propyl dipropylthiocarbamothioate |
| xylachlor | 2-chloro-N-(2,3-dimethylphenyl-N-(1-methylethyl)acetamide |

28

Herbicidal properties of the subject compounds were discovered in a number of greenhouse tests. Test procedures and results follow.

TABLE A
Biological Testing

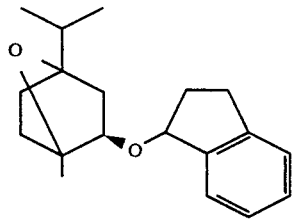

Compound 1

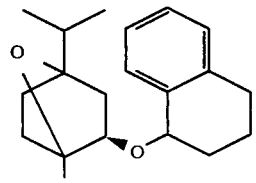

Compound 2

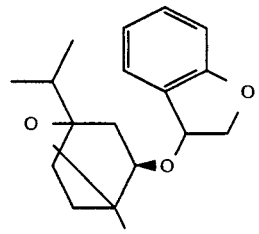

Compound 3

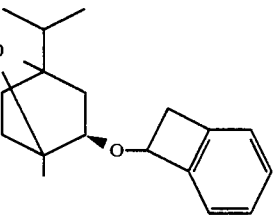

Compound 4

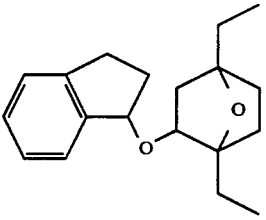

Compound 5

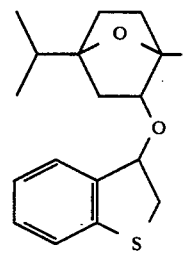

Compound 6

TABLE A-continued
Biological Testing

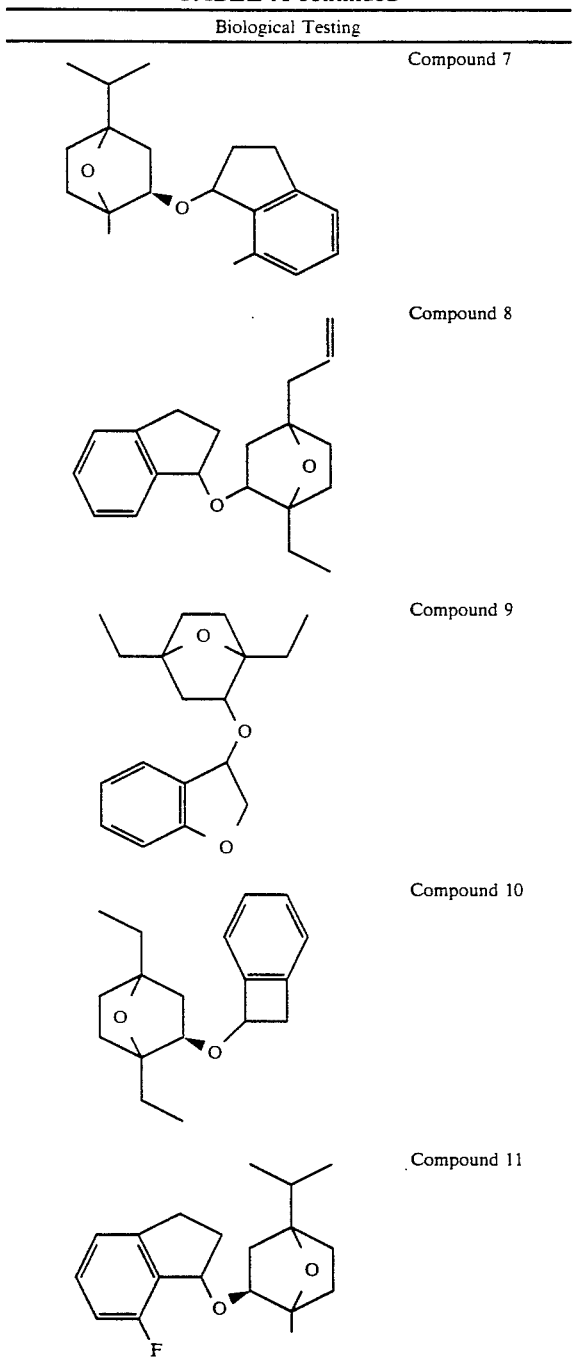

Compound 7

Compound 8

Compound 9

Compound 10

Compound 11

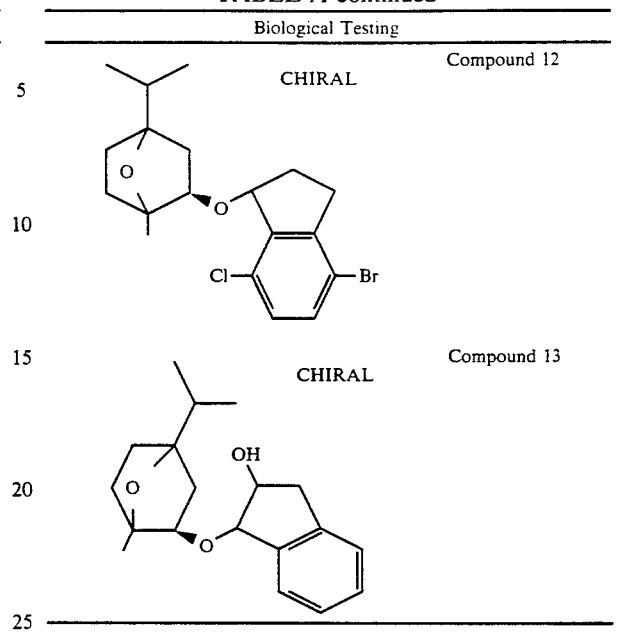

Compound 12
CHIRAL

Compound 13
CHIRAL

TEST A

Seeds of barley (*Hordeum vulgare*), barnyardgrass (*Echinochloa crus-galli*), cheatgrass (*Bromus secalinus*), cocklebur (*Xanthium pensylvanicum*), corn (*Zea mays*), cotton (*Gossypium hirsutum*), crabgrass (Digitaria spp.), giant foxtail (*Setaria faberi*), morningglory (Ipomoea spp.), rice (*Oryza sativa*), sorghum (*Sorghum bicolor*), soybean (*Glycine max*), sugar beet (*Beta vulgaris*), velvetleaf (*Abutilon theophrasti*), wheat (*Triticum aestivum*), and wild oat (*Avena fatua*) and purple nutsedge (*Cyperus rotundus*) tubers were planted and treated preemergence with test chemicals dissolved in a non-phytotoxic solvent. At the same time, these crop and weed species were also treated with postemergence applications of test chemicals. Plants ranged in height from two to eighteen cm (two to three leaf stage) for postemergence treatments. Treated plants and controls were maintained in a greenhouse for approximately sixteen days, after which all species were compared to controls and visually evaluated. Plant response ratings, summarized in Table A, are based on a scale of 0 to 10 where 0 is no effect and 10 is complete control. A dash (—) response means no test result. The accompanying descriptive symbols have the following meanings:

B = burn injury;
C = chlorosis/necrosis;
E = inhibition of emergence;
G = growth retardation;
H = formative effect;
P = terminal bud injury; and
S = albinism.

TABLE A

| | POSTEMERGENCE | | | | | | | | | | | |
|---|---|---|---|---|---|---|---|---|---|---|---|---|
| | Cmpd 1 | | Cmpd 2 | | Cmpd 3 | Cmpd 4 | | Cmpd 5 | | Cmpd 6 | | Cmpd 7 | |
| RATE (g/ha) | 400 | 100 | 400 | 100 | 100 | 400 | 100 | 400 | 50 | 400 | 100 | 400 | 100 |
| Barley | 0 | 0 | 0 | 0 | 0 | 0 | 0 | 0 | 0 | 0 | 0 | 0 | 0 |
| Barnyardgrass | 9H | 0 | 5H | 0 | 9H | 5C,9H | 4H | 9C | 2H | 5H | 0 | 3H | 0 |
| Cheatgrass | 2G | 0 | 0 | 0 | 0 | 0 | 0 | 2G | 0 | 0 | 0 | 0 | 0 |
| Cocklebur | 2H | 0 | 1C | 1C | 1H | 3C,5H | 2C | 2C,4H | 2C | 2C | 1C | 1C,3G | 0 |
| Corn | 2G | 0 | 0 | 0 | 2G | 2C,6G | 0 | 2C,2G | 0 | 0 | 0 | 0 | 0 |
| Cotton | 0 | 0 | 0 | 0 | 0 | 0 | 0 | 7H | 0 | 6H | 0 | 0 | 0 |

TABLE A-continued

| | Cmpd 1 | | Cmpd 2 | | Cmpd 3 | | Cmpd 4 | | Cmpd 5 | | Cmpd 6 | | Cmpd 7 | |
|---|---|---|---|---|---|---|---|---|---|---|---|---|---|---|
| Crabgrass | 8H | 5G | 2S,5G | 0 | 0 | 9H | 4H | 9H | 8H | 0 | 0 | 7H | 0 |
| Giant foxtail | 9H | 5H | 3G | 0 | 8H | 9H | 9H | 9H | 7H | 0 | 0 | 3G | 0 |
| Morningglory | 0 | 0 | 0 | 0 | 2C | 0 | 0 | 0 | 0 | 0 | 0 | 0 | 0 |
| Nutsedge | 0 | 0 | 0 | 0 | 3G | 0 | 0 | 2C,3G | 0 | 0 | 0 | 0 | 0 |
| Rice | 3G | 0 | 0 | 0 | 0 | 0 | 0 | 0 | 0 | 1C | 0 | 0 | 0 |
| Sorghum | 2G | 0 | 0 | 0 | 0 | 3G | 0 | 0 | 0 | 0 | 0 | 0 | 0 |
| Soybean | 2H | 0 | 0 | 0 | 2H | 0 | 0 | 4H | 0 | 1C,7G | 0 | 0 | 0 |
| Sugar beet | 7G | 0 | 0 | 0 | 0 | 0 | 0 | 0 | 0 | 0 | 0 | 0 | 0 |
| Velvetleaf | 5G | 5G | 1C,4G | 3G | 1C,3G | 4H | 0 | 6H | 0 | 4G | 2G | 0 | 0 |
| Wheat | 2G | 0 | 0 | 0 | 2G | 0 | 0 | 0 | 0 | 0 | 0 | 0 | 0 |
| Wild oat | 5G | 0 | 0 | 0 | 0 | 0 | 0 | 0 | 0 | 0 | 0 | 0 | 0 |

| | Cmpd 8 | | Cmpd 9 | | Cmpd 10 | | Cmpd 11 | | Cmpd 12 | | Cmpd 13 | |
|---|---|---|---|---|---|---|---|---|---|---|---|---|
| RATE (g/ha) | 400 | 100 | 400 | 100 | 400 | 100 | 400 | 100 | 400 | 100 | 400 | 100 |
| Barley | 0 | 0 | 8H | 2G | 8G | 0 | 0 | 0 | 0 | 0 | 0 | 0 |
| Barnyardgrass | 9C | 3C,9H | 9C | 9C | 9C | 4C,9G | 3C,9H | 8H | 0 | 0 | 1H | 0 |
| Cheatgrass | 2G | 0 | 9H | 2G | 9G | 1C | 3G | 2G | 0 | 0 | 0 | 0 |
| Cocklebur | 2C | 1C | 2C,6H | 2C | 2C,5H | 1C,2H | 3C | 2C | 1C | 0 | — | 0 |
| Corn | 0 | 0 | 3C,7H | 3C,5H | 3C,8H | 5H | 2G | 0 | 0 | 0 | 0 | 0 |
| Cotton | 8H | 0 | 3H | 3H | 10P,8G | 0 | 2C | 0 | 0 | 0 | 0 | 0 |
| Crabgrass | 9H | 9H | 9H | 9H | 9H | 9H | 9G | 9G | 0 | 0 | 0 | 0 |
| Giant foxtail | 4C,9H | 3C,9H | 5C,9H | 9H | 4C,9G | 4C,9G | 9G | 2G | 2G | 0 | 3G | 0 |
| Morningglory | 0 | 0 | 1H | 0 | 1H | 0 | 0 | 0 | 0 | 0 | 0 | 0 |
| Nutsedge | 0 | 0 | 3C,9H | 0 | — | 0 | — | 0 | 0 | 0 | 0 | 0 |
| Rice | 0 | 0 | 9C | 2G | 8G | 0 | 0 | 0 | 0 | 0 | 0 | 0 |
| Sorghum | 0 | 0 | 5H | 3H | 8H | 0 | 0 | 0 | 0 | 0 | 0 | 0 |
| Soybean | 1C,3H | 1H | 6C,9H | 6H | 6H | 0 | 1C | 0 | 0 | 0 | 0 | 0 |
| Sugar beet | 5H | 2H | 5C,9H | 0 | 6H | 1H | 0 | 0 | 0 | 0 | 0 | 0 |
| Velvetleaf | 3C,7H | 1H | 3C,9H | 6H | 8H | 7H | 2C,6H | 2C,3H | 0 | 0 | 0 | 0 |
| Wheat | 0 | 0 | 9G | 2G | 2G | 0 | 0 | 0 | 0 | 0 | 0 | 0 |
| Wild oat | 0 | 0 | 9H | 4G | 5H | 2G | 0 | 0 | 0 | 0 | 0 | 0 |

| PREEMERGENCE | | | | | | | | | | | | | |
|---|---|---|---|---|---|---|---|---|---|---|---|---|---|
| | Cmpd 1 | | Cmpd 2 | | Cmpd 3 | | Cmpd 4 | | Cmpd 5 | | Cmpd 6 | | Cmpd 7 | |
| RATE (g/ha) | 400 | 100 | 400 | 100 | 100 | 400 | 100 | 400 | 50 | 400 | 100 | 400 | 100 |
| Barley | 0 | 0 | 0 | 0 | 0 | 7H | 0 | 0 | 0 | 0 | 0 | 0 | 0 |
| Barnyardgrass | 10H | 10H | 10H | 10H | 10H | 10H | 10H | 10H | 10H | 10H | 8H | 10H | 7H |
| Cheatgrass | 9E | 7G | 4G | 0 | 3G | 2G | 0 | 3G | 2G | 2G | 0 | 4G | 0 |
| Cocklebur | 0 | 0 | 1C | 0 | 2G | 0 | 0 | 3H | — | 5G | 0 | 0 | 0 |
| Corn | 9H | 2G | 2G | 0 | 2G | 3C,6H | 4H | 5C,8H | 0 | 3G | 0 | 0 | 0 |
| Cotton | 0 | 0 | 0 | 0 | 0 | 0 | 0 | 0 | 0 | 0 | 0 | 0 | 0 |
| Crabgrass | 10H | 10H | 9H | 6G | 4C,9H | 9H | 9H | 10H | 10H | 2G | 0 | 9H | 5G |
| Giant foxtail | 10H | 10H | 9H | 8G | 9H | 10H | 5C,9H | 10H | 10H | 9H | 3G | 9H | 7G |
| Morningglory | 0 | 0 | 0 | 0 | 0 | 0 | 0 | 0 | 0 | 2H | 0 | 0 | 0 |
| Nutsedge | 10E | 0 | 0 | 0 | 0 | 0 | 0 | 0 | 0 | 0 | 0 | 0 | 0 |
| Rice | 5G | 0 | 0 | 0 | 0 | 0 | 0 | 3G | 0 | 0 | 0 | 0 | 0 |
| Sorghum | 10H | 9H | 2C,6G | 0 | 8H | 3C,9H | 6H | 3C,7H | 2G | 5G | 0 | 0 | 0 |
| Soybean | 0 | 0 | 0 | 0 | 0 | 2G | 0 | 0 | 0 | 0 | 0 | 0 | 0 |
| Sugar beet | 5H | 0 | 4G | 0 | 0 | 0 | 0 | 0 | 0 | 0 | 0 | 0 | 0 |
| Velvetleaf | 6H | 2H | 7G | 4G | 8H | 7H | 4H | 8H | 3H | 7H | 0 | 3C,5H | 1H |
| Wheat | 0 | 0 | 0 | 0 | 3G | 0 | 0 | 5H | 0 | 0 | 0 | 0 | 0 |
| Wild oat | 6G | 0 | 3C,7H | 2C,5G | 0 | 9H | 2G | 7H | 0 | 0 | 0 | 2C | 0 |

| | Cmpd 8 | | Cmpd 9 | | Cmpd 10 | | Cmpd 11 | | Cmpd 12 | | Cmpd 13 | |
|---|---|---|---|---|---|---|---|---|---|---|---|---|
| RATE (g/ha) | 400 | 100 | 400 | 100 | 400 | 100 | 400 | 100 | 400 | 100 | 400 | 100 |
| Barley | 0 | 0 | 8H | 0 | 8H | 0 | 3G | 0 | 0 | 0 | 0 | 0 |
| Barnyardgrass | 10H | 10H | 10H | 10H | 10H | 10H | 10H | 9H | 0 | 0 | 2C,8G | 2C,5G |
| Cheatgrass | 0 | 0 | 9H | 6H | 9H | 9G | 6G | 5G | 0 | 0 | 0 | 0 |
| Cocklebur | 0 | 0 | 0 | 0 | 5G | 0 | 1C,2H | 0 | 0 | 0 | 0 | 0 |
| Corn | 0 | 0 | 4C,8H | 4G | 10H | 3C,8H | 4C,8H | 3G | 0 | 0 | 0 | 0 |
| Cotton | 0 | 0 | 8H | 0 | 0 | 0 | 2G | 0 | 0 | 0 | 0 | 0 |
| Crabgrass | 10H | 9H | 10H | 10H | 10H | 10H | 10H | 8H | 3G | 0 | 5G | 0 |
| Giant foxtail | 10H | 10H | 10H | 10H | 10H | 10H | 10H | 8H | 4G | 0 | 3G | 0 |
| Morningglory | 0 | 0 | 0 | 0 | 0 | 0 | 0 | 0 | 0 | 0 | 0 | 0 |
| Nutsedge | 0 | 0 | 3C,9G | 5G | 2C,8G | 10E | 0 | 0 | 0 | 0 | 10E | 0 |
| Rice | 0 | 0 | 3G | 2G | 8H | 0 | 2C,2G | 0 | 0 | 0 | 0 | 0 |
| Sorghum | 3C,8H | 0 | 9H | 9H | 10H | 3C,9H | 4C,8G | 4G | 0 | 0 | 2G | 0 |
| Soybean | 0 | 0 | 9H | 8H | 4H | 0 | 0 | 0 | 0 | 0 | 0 | 0 |
| Sugar beet | 3H | 2H | 3H | 2H | 4H | 2H | 0 | 0 | 0 | 0 | 2G | 0 |
| Velvetleaf | 8H | 6H | 4C,9H | 8H | 5H | 2C,6H | 5H | 2H | 0 | 0 | 4H | 0 |
| Wheat | 0 | 0 | 7G | 3G | 2C,5G | 0 | 2G | 0 | 0 | 0 | 0 | 0 |
| Wild oat | 0 | 0 | 8H | 2G | 9H | 2G | 2C,8H | 2H | 0 | 0 | 0 | 0 |

TEST B

Seeds of barley (*Hordeum vulgare*), barnyardgrass (*Echinochloa crus-galli*), blackgrass (*Alopecurus myosuroides*), chickweed (*Stellaria media*), cocklebur (*Xanthium pensylvanicum*), corn (*Zea mays*), cotton (*Gossypium hirsutum*), crabgrass (Digitaria spp.), downy brome (*Bromus tectorum*), giant foxtail (*Setaria faberi*), green foxtail (*Setaria viridis*), jimsonweed (*Datura stramonium*), johnsongrass (*Sorghum halepense*), lambsquarters (*Chenopodium album*), morningglory (Ipomoea spp.), rape (*Brassica napus*), rice (*Oryza sativa*), sicklepod (*Cas-* sia obtusifolia), soybean (Glycine max), sugar beet (Beta vulgaris), teaweed (Sida spinosa), velvetleaf (Abutilon effect and 100 is complete control. A dash (—) response means no test result.

TABLE B

| | POSTEMERGENCE | | | | | | | | | | | | | |
|---|---|---|---|---|---|---|---|---|---|---|---|---|---|---|
| | Cmpd 1 | | Cmpd 2 | | | | Cmpd 4 | | | | Cmpd 5 | | | |
| RATE (g/ha) | 500 | 250 | 250 | 125 | 62 | 31 | 250 | 125 | 62 | 31 | 250 | 125 | 62 | 31 |
| Barley | 0 | 0 | 0 | 0 | 0 | 0 | 30 | 0 | 0 | 0 | 0 | 0 | 0 | 0 |
| Barnyardgrass | 85 | 80 | 90 | 90 | 90 | 50 | 70 | 65 | 60 | 40 | 60 | 50 | 30 | 0 |
| Blackgrass | 30 | 20 | 0 | 0 | 0 | 0 | 100 | 90 | 70 | 40 | 30 | 0 | 0 | 0 |
| Chickweed | 0 | 0 | 0 | 0 | 0 | 0 | 0 | 0 | 0 | 0 | 0 | 0 | 0 | 0 |
| Cocklebur | 0 | 0 | 0 | 0 | 0 | 0 | 30 | 0 | 0 | 0 | 0 | 0 | 0 | 0 |
| Corn | 20 | 0 | 30 | 20 | 0 | 0 | 0 | 0 | 0 | 0 | 0 | 0 | 0 | 0 |
| Cotton | 0 | 0 | 0 | 0 | 0 | 0 | 0 | 0 | 0 | 0 | 0 | 0 | 0 | 0 |
| Crabgrass | 90 | 50 | 70 | 20 | 0 | 0 | 90 | 80 | 70 | 60 | 70 | — | 30 | 0 |
| Downy brome | 0 | 0 | 0 | 0 | 0 | 0 | 0 | 0 | 0 | 0 | 0 | 0 | 0 | 0 |
| Giant foxtail | 90 | 90 | 40 | 30 | 0 | 0 | 90 | 60 | 30 | 0 | 90 | 80 | 60 | 30 |
| Green foxtail | 40 | 30 | 40 | 20 | 0 | 0 | 70 | 60 | 40 | 30 | 60 | 0 | 0 | 0 |
| Jimsonweed | 0 | 0 | 0 | 0 | 0 | 0 | 50 | 30 | 0 | 0 | 30 | 0 | 0 | 0 |
| Johnsongrass | 30 | 20 | 0 | 0 | 0 | 0 | 0 | 0 | 0 | 0 | 30 | 0 | 0 | 0 |
| Lambsquarters | 40 | 30 | 80 | 20 | 0 | 0 | 80 | 70 | 60 | 30 | 90 | 60 | 30 | 0 |
| Morningglory | 0 | 0 | 0 | 0 | 0 | 0 | 50 | 0 | 0 | 0 | 0 | 0 | 0 | 0 |
| Nutsedge | 60 | 0 | 0 | 0 | 0 | 0 | — | — | — | — | — | — | — | — |
| Rape | 0 | 0 | 30 | 20 | 0 | 0 | 80 | 50 | 0 | 0 | 0 | 0 | 0 | 0 |
| Rice | 0 | 0 | 0 | 0 | 0 | 0 | 0 | 0 | 0 | 0 | 70 | 20 | 0 | 0 |
| Sicklepod | 0 | 0 | 0 | 0 | 0 | 0 | 30 | 0 | 0 | 0 | 30 | 0 | 0 | 0 |
| Soybean | 0 | 0 | 0 | 0 | 0 | 0 | 0 | 0 | 0 | 0 | 0 | 0 | 0 | 0 |
| Sugar beet | 60 | 20 | 0 | 0 | 0 | 0 | 0 | 0 | 0 | 0 | 30 | 0 | 0 | 0 |
| Teaweed | 0 | 0 | 0 | 0 | 0 | 0 | 0 | 0 | 0 | 0 | 0 | 0 | 0 | 0 |
| Velvetleaf | 60 | 40 | 40 | 20 | 0 | 0 | 70 | 30 | 30 | 0 | 30 | 30 | 0 | 0 |
| Wheat | 0 | 0 | 0 | 0 | 0 | 0 | 0 | 0 | 0 | 0 | 0 | 0 | 0 | 0 |
| Wild buckwheat | 0 | 0 | 0 | 0 | 0 | 0 | 30 | 0 | 0 | 0 | 0 | 0 | 0 | 0 |
| Wild oat | 30 | 20 | 0 | 0 | 0 | 0 | 0 | 0 | 0 | 0 | 0 | 0 | 0 | 0 |

| | PREEMERGENCE | | | | | | | | | | | | | |
|---|---|---|---|---|---|---|---|---|---|---|---|---|---|---|
| | Cmpd 1 | | | | Cmpd 2 | | | | Cmpd 4 | | | | Cmpd 5 | | | |
| RATE (g/ha) | 500 | 250 | 125 | 62 | 250 | 125 | 62 | 31 | 250 | 125 | 62 | 31 | 250 | 125 | 62 | 31 |
| Barley | 0 | 0 | 0 | 0 | 0 | 0 | 0 | 0 | 50 | 30 | 0 | 0 | 0 | 0 | 0 | 0 |
| Barnyardgrass | 100 | 100 | 100 | 30 | 100 | 100 | 100 | 100 | 100 | 100 | 100 | 100 | 100 | 100 | 100 | 100 |
| Blackgrass | 100 | 100 | 70 | 40 | 40 | 30 | 30 | 30 | 100 | 100 | 60 | 60 | 100 | 100 | 100 | 85 |
| Chickweed | 0 | 0 | 0 | 0 | 0 | 0 | 0 | 0 | 70 | 70 | 30 | 0 | 30 | 20 | 0 | 0 |
| Cocklebur | 20 | 0 | 0 | 0 | 0 | — | 0 | 0 | 100 | 0 | 0 | — | 50 | 0 | — | — |
| Corn | 30 | 20 | 20 | 0 | 0 | 0 | 0 | 0 | 100 | 80 | 50 | 20 | 70 | 50 | 0 | 0 |
| Cotton | 0 | 0 | 0 | 0 | 0 | 0 | 0 | 0 | 30 | 30 | 0 | 0 | 30 | 20 | 0 | — |
| Crabgrass | 100 | 100 | 100 | 100 | 100 | 100 | 100 | 90 | 100 | 100 | 100 | 100 | 100 | 100 | 100 | 100 |
| Downy brome | 90 | 90 | 90 | 30 | 0 | 0 | 0 | 0 | 100 | 100 | 40 | 20 | 60 | 40 | 0 | 0 |
| Giant foxtail | 100 | 100 | 100 | 50 | 100 | 100 | 80 | 70 | 100 | 100 | 100 | 100 | 100 | 100 | 100 | 100 |
| Green foxtail | 100 | 100 | 100 | 100 | 90 | 80 | 70 | 30 | 100 | 100 | 100 | 100 | 100 | 100 | 100 | 100 |
| Jimsonweed | 0 | 0 | 0 | 0 | 0 | 0 | 0 | 0 | 80 | 40 | 30 | 0 | 0 | 0 | 0 | 0 |
| Johnsongrass | 80 | 70 | 70 | 40 | 50 | 30 | 20 | 20 | 100 | 80 | 75 | 40 | 100 | 100 | 100 | 100 |
| Lambsquarters | 80 | 80 | — | 70 | 90 | 80 | 50 | 50 | 0 | 0 | 0 | 0 | 80 | 60 | 50 | 30 |
| Morningglory | 0 | 0 | 0 | 0 | 0 | 0 | 0 | 0 | 0 | 0 | 0 | 0 | 0 | 0 | 0 | 0 |
| Nutsedge | 30 | 0 | 0 | 0 | 0 | 0 | 0 | 0 | 20 | 0 | 0 | 0 | — | — | — | — |
| Rape | 20 | 0 | 0 | 0 | 0 | 0 | 0 | 0 | 40 | 0 | 0 | 0 | 0 | 0 | 0 | 0 |
| Rice | 40 | 10 | 0 | 0 | 30 | 0 | 0 | 0 | 40 | 0 | 0 | 0 | 0 | 0 | 0 | 0 |
| Sicklepod | 0 | 0 | 0 | 0 | 100 | 40 | 0 | 0 | 50 | 30 | 0 | 0 | 50 | 30 | 0 | 0 |
| Soybean | 0 | 0 | 0 | 0 | 0 | 0 | 0 | 0 | 0 | 0 | 0 | 0 | 20 | 0 | 0 | 0 |
| Sugar beet | 30 | 20 | 0 | 0 | 0 | 0 | 0 | 0 | — | 50 | 30 | 30 | 50 | 30 | 0 | 0 |
| Teaweed | 50 | 40 | 30 | 20 | 60 | 60 | 60 | 0 | 80 | — | 70 | 0 | 70 | 30 | 0 | 0 |
| Velvetleaf | 80 | 70 | 40 | 20 | 70 | 50 | 20 | 0 | 90 | 80 | 50 | 0 | 100 | 100 | 80 | 30 |
| Wheat | 0 | 0 | 0 | 0 | 0 | 0 | 0 | 0 | 30 | 0 | 0 | 0 | 0 | 0 | 0 | 0 |
| Wild buckwheat | 90 | 60 | 40 | 30 | 0 | 0 | 0 | 0 | 0 | 0 | 0 | 0 | 0 | 0 | 0 | 0 |
| Wild oat | 100 | 60 | 40 | 30 | 0 | 0 | 0 | 0 | 40 | 30 | 30 | 0 | 40 | 30 | 20 | 0 | theophrasti), wheat (Triticum aestivum), wild buckwheat (Polygonum convolvulus), and wild oat (Avena fatua) and purple nutsedge (Cyperus rotundus) tubers were planted and treated preemergence with test chemicals dissolved in a non-phytotoxic solvent. At the same time, these crop and weed species were also treated with postemergence applications of test chemicals. Plants ranged in height from two to eighteen cm (two to three leaf stage) for postemergence treatments. Treated plants and controls were maintained in a greenhouse for approximately 24 days, after which all species were compared to controls and visually evaluated. Preemergence and postemergence application rates for each compound are listed in Table B. Plant response ratings, summarized in Table B, are based on a scale of 0 to 100 where 0 is no

TEST C

Plastic pots were partially filled with silt loam soil. The soil was then saturated with water. Indica and Japonica rice (Oryza sativa) seedlings at the 2.0 to 2.5 leaf stage, seeds of barnyardgrass (Echinochloa crusgalli), bulrush (Scirpus mucronatus), and umbrella sedge (Cyperus difformis), and sprouted tubers of arrowhead (Sagittaria spp). and waterchestnut (Eleocharis spp.) were planted into this soil. Several days after planting, water levels were raised to 3 cm above the soil surface and maintained at this level throughout the test. Chemical treatments were formulated in a non-phytotoxic solvent and applied directly to the paddy water. Treated plants and controls were maintained in a greenhouse for approximately 21 days, after which all species were compared to controls and visually evaluated. Plant response ratings, summarized in Table C, are based on a scale of 0 to 100 where 0 is no effect and 100 is complete control. A dash (—) response means no test result.

sian thistle (*Salsola kali*), scentless chamomile (*Matricaria inodora*), sugar beet (*Beta vulgaris*), spring and winter wheat (*Triticum aestivum*), wild buckwheat (*Polygonum convolvulus*), and wild oat (*Avena fatua*) were planted and treated preemergence with test chemicals dissolved in a non-phytotoxic solvent. Postemergence applications of test chemicals were also applied to these same crop and weed species. Plants ranged in height from

TABLE C

|  | Cmpd 1 | | | | | Cmpd 2 | | | | | Cmpd 3 | | | | |
|---|---|---|---|---|---|---|---|---|---|---|---|---|---|---|---|
| RATE (g/ha) | 1000 | 500 | 250 | 125 | 64 | 1000 | 500 | 250 | 125 | 64 | 500 | 250 | 125 | 64 | 32 |
| Arrowhead | 70 | 90 | 70 | 60 | 30 | 0 | 0 | 0 | 0 | 0 | — | — | — | — | — |
| Barnyardgrass | 100 | 100 | 100 | 100 | 100 | 100 | 100 | 100 | 100 | 100 | 100 | 100 | 100 | 95 | 95 |
| Bulrush | 95 | 95 | 95 | 90 | 0 | 90 | 90 | 0 | 0 | 0 | 90 | 90 | 90 | 90 | 90 |
| Rice (Indica) | 50 | 20 | 0 | 0 | 0 | 30 | 30 | 0 | 0 | 0 | 80 | 80 | 40 | 30 | 0 |
| Rice (Japonica) | 30 | 20 | 0 | 0 | 0 | 20 | 0 | 0 | 0 | 0 | 90 | 80 | 50 | 20 | 0 |
| Umbrella sedge | 100 | 100 | 100 | 100 | 95 | 100 | 100 | 100 | 100 | 0 | 100 | 100 | 100 | 100 | 100 |
| Waterchestnut | 100 | 100 | 100 | 100 | 100 | 100 | 70 | 100 | 0 | 0 | 90 | 60 | 50 | 70 | 40 |
|  | Cmpd 5 | | | | | Cmpd 7 | | | | | Cmpd 10 | | | | |
| Rate (g/ha) | 500 | 250 | 125 | 64 | 32 | 500 | 250 | 125 | 64 | 32 | 500 | 250 | 125 | 64 | 32 |
| Arrowhead | 90 | 0 | 0 | 0 | 0 | 0 | 0 | 0 | 0 | 0 | 95 | 95 | 60 | 95 | 0 |
| Barnyardgrass | 100 | 100 | 100 | 100 | 100 | 100 | 100 | 100 | 100 | 70 | 100 | 100 | 100 | 100 | 100 |
| Bulrush | 95 | 95 | 95 | 95 | 80 | 95 | 0 | 0 | 0 | 0 | 95 | 95 | 90 | 60 | 0 |
| Rice (Indica) | 50 | 30 | 20 | 0 | 0 | 0 | 0 | 0 | 0 | 0 | 60 | 40 | 0 | 0 | 0 |
| Rice (Japonica) | 40 | 30 | 0 | 0 | 0 | 0 | 0 | 0 | 0 | 0 | 70 | 50 | 0 | 0 | 0 |
| Umbrella sedge | 100 | 100 | 100 | 100 | 100 | 100 | 100 | 100 | 100 | 95 | 100 | 100 | 100 | 100 | 100 |
| Waterchestnut | 95 | 0 | 0 | 0 | 0 | 0 | 0 | 0 | 0 | 0 | 95 | 95 | 95 | 0 | 0 |

TEST D

Seeds of spring and winter barley (*Hordeum vulgare*), black nightshade (*Solanum nigrum*), blackgrass (*Alopercurus myosuroides*), bluegrass (*Poa annua*), catchweed bedstraw (*Gallium aparine*), cheatgrass (*Bromus secalinus*), downy brome (*Bromus tectorum*), field pennycress (*Thlaspi arvense*), field violet (*Viola arvensis*), green foxtail (*Setaria viridis*), Italian ryegrass (*Lolium multiflorum*), ivyleaf speedwell (*Veronica hederaefolia*), jointed goatgrass (*Aegilops cylindrica*), kochia (*Kochia scoparia*), lambsquarters (*Chenopodium album*), Persian speedwell (*Veronica persica*), rape (*Brassica napus*), Rustwo to twenty-four cm (two to three leaf stage) for postemergence treatments. Blackgrass and wild oat were treated postemergence at two growth stages—the first stage being at two to three leaves and the second stage being approximately at four leaves or in the initial stages of tillering. Treated plants and controls were maintained in a greenhouse for approximately 21 days, after which all species were compared to controls and visually evaluated. Rates of application of each compound are listed in Table D. Plant response ratings, summarized in Table D, are based on a scale of 0 to 100 where 0 is no effect and 100 is complete control.

TABLE D

|  | Cmpd 1 | | | | Cmpd 2 | | | |
|---|---|---|---|---|---|---|---|---|
| RATE (g/ha) | 500 | 250 | 125 | 64 | 500 | 250 | 125 | 64 |
| POSTEMERGENCE | | | | | | | | |
| Barley (Spring) | 0 | 0 | 0 | 0 | 0 | 0 | 0 | 0 |
| Barley (Winter) | 0 | 0 | 0 | 0 | 0 | 0 | 0 | 0 |
| Black nightshade | 10 | 0 | 0 | 0 | 10 | 0 | 0 | 0 |
| Blackgrass | 10 | 0 | 0 | 0 | 20 | 0 | 0 | 0 |
| Blackgrass (Stage 2) | 0 | 0 | 0 | 0 | 0 | 0 | 0 | 0 |
| Bluegrass | 50 | 50 | 20 | 0 | 20 | 0 | 0 | 0 |
| Catchweed bedstraw | 0 | 0 | 0 | 0 | 20 | 10 | 0 | 0 |
| Cheatgrass | 0 | 0 | 0 | 0 | 0 | 0 | 0 | 0 |
| Downy brome | 0 | 0 | 0 | 0 | 0 | 0 | 0 | 0 |
| Field pennycress | 10 | 0 | 0 | 0 | 10 | 0 | 0 | 0 |
| Field violet | 0 | 0 | 0 | 0 | 0 | 0 | 0 | 0 |
| Green foxtail | 60 | 60 | 0 | 0 | 20 | 0 | 0 | 0 |
| Italian ryegrass | 0 | 0 | 0 | 0 | 0 | 0 | 0 | 0 |
| Ivyleaf speedwell | 0 | 0 | 0 | 0 | 0 | 0 | 0 | 0 |
| Jointed goatgrass | 0 | 0 | 0 | 0 | 0 | 0 | 0 | 0 |
| Kochia | 0 | 0 | 0 | 0 | 20 | 0 | 0 | 0 |
| Lambsquarters | 10 | 0 | 0 | 0 | 10 | 0 | 0 | 0 |
| Persian speedwell | 0 | 0 | 0 | 0 | 0 | 0 | 0 | 0 |
| Rape | 50 | 10 | 0 | 0 | 10 | 0 | 0 | 0 |
| Russian thistle | 0 | 0 | 0 | 0 | 0 | 0 | 0 | 0 |
| Scentless chamomile | 0 | 0 | 0 | 0 | 0 | 0 | 0 | 0 |
| Sugar beet | 10 | 0 | 0 | 0 | 20 | 0 | 0 | 0 |
| Wheat (Spring) | 0 | 0 | 0 | 0 | 0 | 0 | 0 | 0 |
| Wheat (Winter) | 0 | 0 | 0 | 0 | 0 | 0 | 0 | 0 |
| Wild buckwheat | 0 | 0 | 0 | 0 | 0 | 0 | 0 | 0 |
| Wild oat | 0 | 0 | 0 | 0 | 0 | 0 | 0 | 0 |
| Wild oat (Stage 2) | 0 | 0 | 0 | 0 | 0 | 0 | 0 | 0 |
| PREEMERGENCE | | | | | | | | |

TABLE D-continued

| RATE (g/ha) | Cmpd 1 | | | | Cmpd 2 | | | |
|---|---|---|---|---|---|---|---|---|
| | 500 | 250 | 125 | 64 | 500 | 250 | 125 | 64 |
| Barley (Spring) | 20 | 10 | 0 | 0 | 0 | 0 | 0 | 0 |
| Barley (Winter) | 20 | 0 | 0 | 0 | 0 | 0 | 0 | 0 |
| Black nightshade | 0 | 0 | 0 | 0 | 0 | 0 | 0 | 0 |
| Blackgrass | 100 | 100 | 20 | 0 | 90 | 30 | 10 | 10 |
| Blackgrass (Stage 2) | | | | | | | | |
| Bluegrass | 100 | 100 | 50 | 10 | 100 | 90 | 60 | 50 |
| Catchweed bedstraw | 20 | 0 | 0 | 0 | 0 | 0 | 0 | 0 |
| Cheatgrass | 70 | 20 | 0 | 0 | 10 | 0 | 0 | 0 |
| Downy brome | 90 | 60 | 50 | 10 | 70 | 20 | 0 | 0 |
| Field pennycress | 30 | 0 | 0 | 0 | 60 | 50 | 20 | 0 |
| Field violet | 40 | 20 | 20 | 0 | 100 | 70 | 20 | 0 |
| Green foxtail | 100 | 100 | 100 | 100 | 100 | 100 | 100 | 100 |
| Italian ryegrass | 90 | 80 | 20 | 20 | 80 | 60 | 20 | 0 |
| Ivyleaf speedwell | 60 | 0 | 0 | 0 | 50 | 10 | 0 | 0 |
| Jointed goatgrass | 20 | 10 | 0 | 0 | 10 | 0 | 0 | 0 |
| Kochia | 100 | 80 | 40 | 20 | 30 | 20 | 0 | 0 |
| Lambsquarters | 60 | 60 | 50 | 40 | 50 | 50 | 20 | 0 |
| Persian speedwell | 20 | 20 | 0 | 0 | 10 | 0 | 0 | 0 |
| Rape | 50 | 10 | 0 | 0 | 80 | 70 | 60 | 30 |
| Russian thistle | 20 | 0 | 0 | 0 | 10 | 0 | 0 | 0 |
| Scentless chamomile | 40 | 40 | 10 | 10 | 0 | 0 | 0 | 0 |
| Sugar beet | 70 | 40 | 40 | 20 | 70 | 50 | 30 | 30 |
| Wheat (Spring) | 10 | 0 | 0 | 0 | 0 | 0 | 0 | 0 |
| Wheat (Winter) | 20 | 10 | 0 | 0 | 0 | 0 | 0 | 0 |
| Wild buckwheat | 10 | 0 | 0 | 0 | 0 | 0 | 0 | 0 |
| Wild oat | 30 | 0 | 0 | 0 | 10 | 10 | 0 | 0 |

What is claimed is:
1. A compound of Formula I

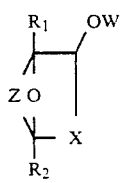
(I)

wherein:
X is $(CH_2)_m$;
Z is $(CR_3R_4)_n$;
m is 1;
n is 2;
$R_1$ is H or a straight-chain $C_1$-$C_3$ alkyl;
$R_2$ is H, $C_1$-$C_6$ alkyl, $C_2$-$C_4$ alkenyl, $C_2$-$C_4$ alkynyl, phenyl or $C_1$-$C_4$ alkyl substituted by halogen, Ph, OH, CN, $OR_a$, $SO_2R_a$, $PhSO_2$, $N_3$, $CO_2R_a$, or $CO_2H$;
$R_3$ is H or $C_1$-$C_3$ alkyl;
$R_4$ is H or $CH_3$;
$R_3$ and $R_4$ can be taken together to form a 5- or 6-membered carbocyclic ring;
W is

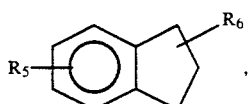
W-1

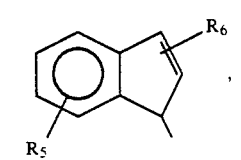
W-2

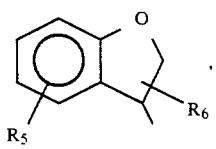
W-3

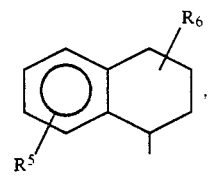
W-6

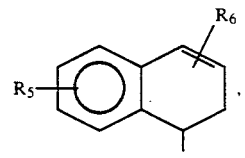
W-13

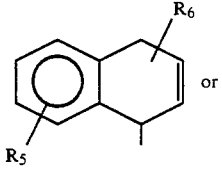
W-14
or

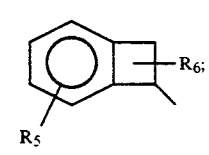
W-15

$R_5$ is H, halogen, $R_a$, $OR_a$, $SR_a$ or CN;
$R_6$ is H, F, Cl, $CH_3$, $OCH_3$, OH or $OR_a$; and
$R_a$ is $C_1$-$C_3$ alkyl.
2. A compound of claim 1 wherein:

$R_2$ is $C_1$–$C_3$ alkyl, $C_2$–$C_3$ alkenyl, $C_2$–$C_3$ alkynyl, or $C_1$–$C_2$ alkyl substituted by OH, CN, $OCH_3$, $SO_2CH_3$, $SO_2Ph$ or $CO_2CH_3$; and $R_5$ is H, F, Cl, Br, $CH_3$, $OCH_3$, $SCH_3$ or CN.

3. A compound of claim 2 wherein:

$R_3$ is H or $CH_3$.

4. The compound of claim 3 which is: 7-oxabicyclo((2.2.1))heptane'2-(2,3-dihydro-1H-inden-1-yloxy)-1-methyl-4-(1-methylethyl)—.

5. The compound of claim 3 which is: 2-(2,3-dihydro-1H-inden-1-yloxy)-1,4-diethyl-7-oxabicyclo[2.2.1]heptane.

6. A composition suitable for controlling the growth of undesired vegetation which comprises an effective amount of a compound of any one of claims 1, 2, 3, 4 and 5 and at least one of the following: surfactant, solid or liquid diluent.

7. A method for controlling the growth of undesired vegetation which comprises applying to the locus to be protected an effective amount of a compound of any one of claims 1, 2, 3, 4 and 5.

8. The method of claim 7 wherein the undesired vegetation is present in rice.

9. A method for controlling the growth of undesired vegetation in rice which comprises applying to the locus to be protected an effective amount of said composition of claim 6.

* * * * *